(12) United States Patent
Chillemi

(10) Patent No.: US 10,790,063 B2
(45) Date of Patent: *Sep. 29, 2020

(54) COMPUTER-AIDED MULTIPLE STANDARD-BASED FUNCTIONAL EVALUATION AND MEDICAL REPORTING SYSTEM

(71) Applicant: Michael Chillemi, Belleville, NJ (US)

(72) Inventor: Michael Chillemi, Belleville, NJ (US)

(*) Notice: Subject to any disclaimer, the term of this patent is extended or adjusted under 35 U.S.C. 154(b) by 219 days.

This patent is subject to a terminal disclaimer.

(21) Appl. No.: 15/902,147

(22) Filed: Feb. 22, 2018

(65) Prior Publication Data
US 2018/0211728 A1    Jul. 26, 2018

Related U.S. Application Data

(63) Continuation of application No. 12/804,646, filed on Jul. 26, 2010, now Pat. No. 9,940,437.

(51) Int. Cl.
| | |
|---|---|
| *G16H 50/30* | (2018.01) |
| *A61B 5/11* | (2006.01) |
| *A61B 5/00* | (2006.01) |
| *G06Q 50/22* | (2018.01) |

(Continued)

(52) U.S. Cl.
CPC ........... *G16H 50/30* (2018.01); *A61B 5/1121* (2013.01); *A61B 5/743* (2013.01); *A61B 5/7435* (2013.01); *G06Q 50/22* (2013.01); *A61B 5/1075* (2013.01); *A61B 5/458* (2013.01); *A61B 5/4566* (2013.01); *A61B 5/4576* (2013.01); *A61B 2560/0223* (2013.01); *G06F 3/048* (2013.01)

(58) Field of Classification Search
CPC ........ G16H 50/20; G16H 10/60; G16H 15/00; G16H 20/13; A61B 5/112; A61B 5/1124; A61B 5/1128; A61B 5/113
USPC .......................................................... 705/2
See application file for complete search history.

(56) References Cited

U.S. PATENT DOCUMENTS

| | | |
|---|---|---|
| 4,367,752 A | 1/1983 | Jimenez et al. |
| 4,665,928 A * | 5/1987 | Linial ................. A61B 5/1121 482/1 |
| 4,858,125 A | 8/1989 | Croce |

(Continued)

FOREIGN PATENT DOCUMENTS

EP    0943290 A1    9/1999

*Primary Examiner* — Hiep V Nguyen
(74) *Attorney, Agent, or Firm* — Thomas A. O'Rourke; Bodner & O'Rourke, LLP

(57) ABSTRACT

A method of performing an objective functional evaluation of a person's physical capacity comprises of a computer program particularly designed to amass and assess test data in accordance with a selected standard. A wide variety of evaluation protocols are incorporated to lead an operator in a step-by-step process. The method includes special testing tools, many of which have been modified to input data directly into the computer diagnostic program. The interface may be a wired or a wireless connection. The software program may use an algorithm to calculate a coefficient of variation for the multiple trials of a test, using the entered data, to providing a determination of validity of the trials. A second algorithm calculates an average result of the condition-specific protocol of tests, after which the software program correlates those average results to a database of normative standards to compute an impairment rating.

14 Claims, 51 Drawing Sheets

(51) Int. Cl.
G06F 3/048 (2013.01)
A61B 5/107 (2006.01)

(56) References Cited

U.S. PATENT DOCUMENTS

| | | |
|---|---|---|
| 5,163,228 A | 11/1992 | Edwards et al. |
| 5,375,610 A | 12/1994 | LaCourse et al. |
| 5,474,083 A | 12/1995 | Church et al. |
| 5,588,444 A | 12/1996 | Petragallo |
| 5,755,675 A | 5/1998 | Sihvonen |
| 5,830,160 A | 11/1998 | Reinkensmeyer |
| 5,833,623 A | 11/1998 | Mann et al. |
| 5,848,594 A | 12/1998 | Matheson |
| 6,607,480 B1 | 8/2003 | Bousseljot et al. |
| 6,827,670 B1 | 12/2004 | Stark et al. |
| 6,866,643 B2 | 3/2005 | Kramer |
| 7,074,168 B1 | 7/2006 | Farnes et al. |
| 7,292,151 B2 | 11/2007 | Ferguson et al. |
| 2004/0215494 A1* | 10/2004 | Wahlbin .......... G06Q 40/02 705/4 |
| 2006/0281983 A1 | 12/2006 | Al-Ali et al. |
| 2007/0032748 A1 | 2/2007 | McNeil et al. |
| 2009/0005709 A1* | 1/2009 | Gagne .......... A61B 5/1071 600/594 |
| 2010/0274141 A1 | 10/2010 | Patangay et al. |
| 2011/0245630 A1 | 10/2011 | St. Pierre et al. |

\* cited by examiner

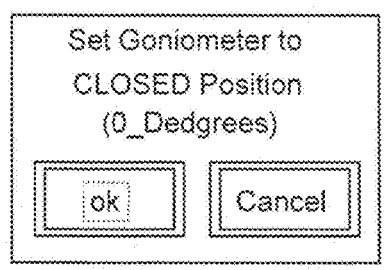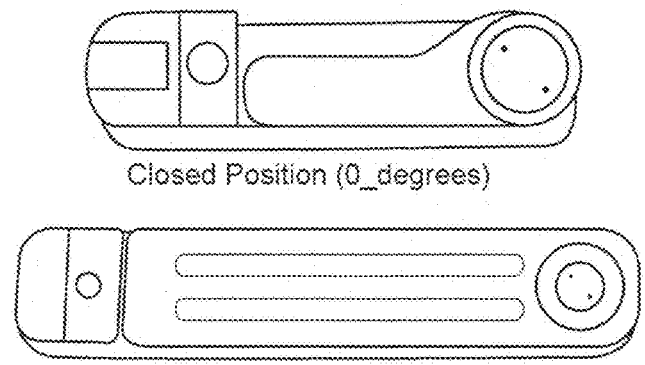
FIG. 15

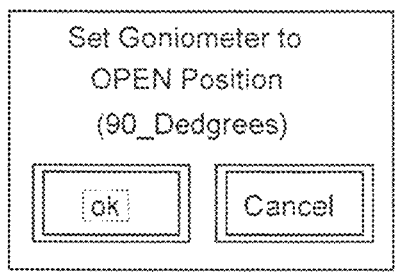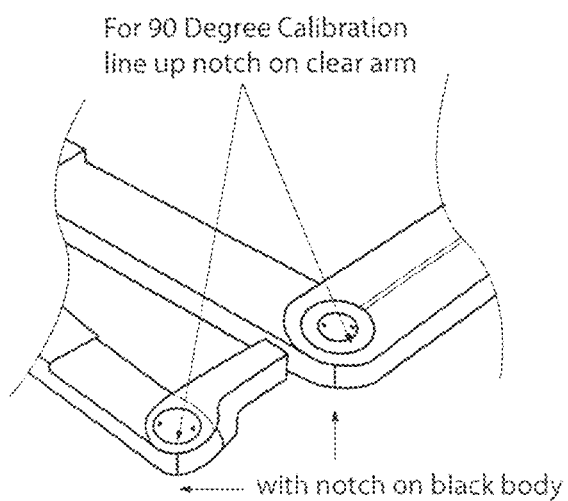
FIG. 18

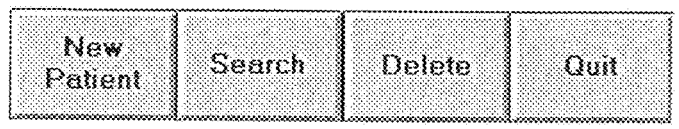
FIG. 38
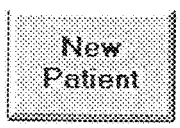
FIG. 39
FIG. 40

Empl/Phys/Ins/Atty Tab of the Patient
Database Screen

History Tab

The Review Screen

Continue Testing Incomplete Tests in a Protocol

Review Results in a Protocol & Make Additional Comments

The Report Screen

Changing Report Options

TABLE 1: PROTOCOLS AND REASONS FOR ORDERING EACH PROTOCOL

| |
|---|
| Ankle/Foot Series Profile- should be ordered if the patient has any of the following conditions: ankle pain, ankle sprain/strain, Achilles bursitis, Achilles tendonitis, flat foot, plantar fasciitis, tarsal tunnel syndrome, pre/post ankle surgery, pre/post rehabilitation. |
| Cervical Series Profile- should be ordered if the patient has any of the following conditions: cervical segmental dysfunction, cervical facet syndrome, cervical disc displacement, cervical disc degeneration, cervical myalgia, cervical myositis, cervical hyper-flexion/extension, cervical nerve injury, cervical segmental dysfunction, cervical plexus compression, cervical radiculitis, cervical sprain/strain, cervico-occipitial syndrome, cervicobrachial syndrome, cerviocranial syndrome, brachial neuritis, pre-post cervical surgery, and pre/post cervical rehabilitation. |
| Cervical/Elbow Series Profile- should be ordered if the patient has a dual diagnosis and you need to determine the extent of the patient's injury. The patient conditions can include but not be limited to: ulnar neuropathy, radial neuropathy, cervical disc displacement, cervical disc degeneration, cervical nerve injury, cerviobrachial syndrome, brachial neuritis, cervical plexus, cervical radiculitis, status pre/post fractures, and rehabilitation progress. |
| Cervical/Wrist Series Profile- should be ordered if the patient has a dual diagnosis and you need to determine the extent of the patient's injury. The patient conditions can include but not be limited to: ulnar neuropathy, radial neuropathy, cervical disc displacement, cervical disc degeneration, cervical nerve injury, cerviobrachial syndrome, brachial neuritis, cervical plexus, cervical radiculitis, pre/post hand surgery, pre/post ankle injury, and fractures. |
| Elbow Series Profile- should be ordered if the patient has any of the following conditions: forearm pain, weakness in the hand, elbow pain, elbow sprain/strain, ulnar neuropathy, radial neuropathy, medial or lateral epicondylitis, pre/post elbow surgery, pre/post elbow rehabilitation. |
| Hip Series Profile- should be ordered if the patient has any of the following conditions: hip pain, hip segmental dysfunction, trauma, hip dysfunction, pre/post hip surgery, & pre/post hip rehabilitation. |
| Knee Series Profile- should be ordered if the patient has any of the following conditions: knee pain, knee sprain/strain, meniscus sprain/tear, liagementous dysfunction, pre/post knee surgery, and pre/post knee rehabilitation. |
| Lumbar Series Profile- should be ordered if the patient has any of the following conditions: back pain, lumbar disc displacement, lumbar disc degeneration, lumbar radiculitis, lumbar segmental dysfunction, lumbosacral dysfunction, sciatic neuritis, pre/post lumbar surgery, and pre/post lumbar rehabilitation. |
| Lower Extremity Series Profile- should be ordered if the patient has any of the following conditions: leg pain, hip pain, knee pain, ankle pain, lower extremity segmental dysfunction, joint disorder at multiple sites, and lower pain. |
| Shoulder Series Profile- should be ordered if the patient has any of the following conditions: shoulder pain, shoulder motion dysfunction, rotator cuff sprain/strain, rotator cuff tears, impingement syndromes, bursitis, tendonitis, double crush syndrome, pre/post cuff surgery, pre/post rehabilitation, and fractures. |
| Thoracic Series Profile- should be ordered if the patient has any of the following conditions: thoracic pain, intercostal neuritis, thoracic segmental dysfunction, thoracolumbar dysfunction, and thoracic disc displacement. |
| Upper Extremity Profile- should be ordered if the patient has any of the following conditions: forearm pain, weakness in the hand, elbow pain, elbow sprain/strain, brachial plexus lesions, carpal tunnel syndrome, ulnar neuropathy, radial neuropathy, medial epicondylitis, lateral epicondylitis, pre/post hand surgery, and pre/post rehabilitation, and fractures |
| Wrist/Carpal Tunnel Series Profile- should be ordered if patient has any of the following conditions: carpal tunnel syndrome, ulnar neuropathy, radial neuropathy, medial epicondylitis, lateral epicondylitis, pre/post hand surgery, and pre/post rehabilitation. |

FIG. 73A

TABLE 2

| Ankle/Foot Series Profile: |
| --- |
| 1. Pain Drawing |
| 2. EG- Ankle Inversion |
| 3. EG- Ankle Eversion |
| 4. EG- Ankle Dorsiflexion |
| 5. EG- Ankle Plantar Flexion |
| 6. EG- Stress Inversion Ankle Plantar Flexion |
| 7. EG- Stress Inversion Ankle Dorsiflexion |
| 8. EG- Stress Inversion Ankle Neutral |
| 9. CX- Great Toe Flexion |
| 10. CX- Great Toe Extension |
| 11. CX- Ankle Dorsiflexion |
| 12. CX- Ankle Plantar flexion Knee Flexed |
| 13. CX- Ankle Plantar flexion |
| 14. CX- Ankle Eversion |
| 15. CX-Ankle Inversion |
| 16. ST- Floor Lift |
| 17. ST- LEG Lift |
| 18. ST- Arm Lift |

FIG. 73B

TABLE 3

| Cervical Series Profile: |
| --- |
| 1. Pain Drawing |
| 2. RM- Cervical Flexion |
| 3. RM- Cervical Extension |
| 4. RM- Cervical Lateral Flexion |
| 5. RM- Cervical Rotation |
| 6. CX- Elbow Extension |
| 7. CX- Elbow Flexion |
| 8. CX- Shoulder Abduction |
| 9. CX- Cervical Rotation |
| 10. CX- Cervical Lateral Flexion |
| 11. CX- Cervical Extension |
| 12. CX- Cervical Flexion |
| 13. CX- Finger Flexion |
| 14. CX- Thumb Opposition |
| 15. PG- Key Pinch |
| 16. PG- Tip Pinch |
| 17. PG- Palmar Pinch |
| 18. HD- Position1 Hand Grip |
| 19. HD- Position Standard Hand Grip |
| 20. HD- Position 3 Hand Grip |
| 21. HD- Position 4 Hand Grip |
| 22. HD- Position 5 Hand Grip |
| 23. ST- Arm Lift |
| 24. ST- High Near |

FIG. 73C

ROM

Cervical Flexion

Cervical Extension

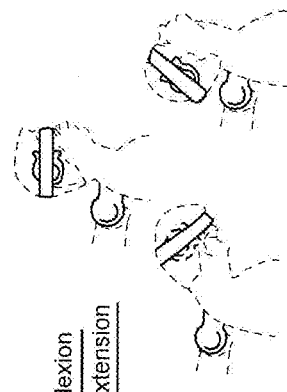

Cervical Flexion

Positioning: with patient seated place inclinometer on top of patients head with orange button facing forward Instruction: "bend your head forward bringing your chin to chest"

Cervical Extension

Positioning: patient seated, place inclinometer on top of patients head with orange button facing back Instruction: "tilt/bring head backward all the way back or look up at the ceiling"

Cervical Lateral Flexion

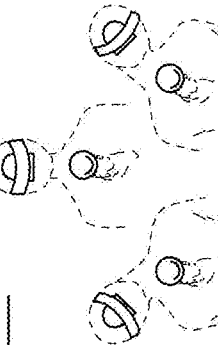

Cervical Lateral Flexion

Positioning: patient seated, inclinometer placed on top of head and orange button facing to the left or right Instruction: "bend their head either left or right" or "bring your left ear to your left Shoulder".

Cervical Rotation

Cervical Rotation

Positioning: patient supine, place inclinometer on patients forehead with the black part of inclinometer facing patients toes Instruction: "turn your head to your left/right"

Muscle Testing

Elbow Extension

Positioning: patient seated, elbow fully flexed and pronated with resistance at the palmar aspect of wrist   Instruction: "push towards me".

Elbow Flexion

Elbow Flexion

Positioning: patient seated, elbow flexed to 90 degrees and fully supinated, with resistance on the palmar aspect of the wrist Instruction: "bend your elbow up"

FIG. 74

TABLE 4

| Carpal Tunnel Series Profile: |
| --- |
| 1. Pain Drawing |
| 2. EG- Wrist Dorsal Flexion |
| 3. EG- Wrist Palmar Flexion |
| 4. EG- Wrist Radial Deviation |
| 5. EG- Wrist Ulnar Deviation |
| 6. EG- Thumb Mp Flexion |
| 7. EG- Thumb Mp Extension |
| 8. EG- Ring Finger Mp Flexion |
| 9. EG- Ring Finger Mp Extension |
| 10. EG- Middle Finger Mp Flexion |
| 11. EG- Middle Finger Mp Extension |
| 12. EG- Little Finger Mp Flexion |
| 13. EG- Little Finger Mp Extension |
| 14. EG- Index Finger Mp Flexion |
| 15. EG- Index Finger Mp Extension |
| 16. CX- Wrist Dorsal Flexion |
| 17. CX- Wrist Palmar Flexion |
| 18. CX- Wrist Radial Deviation |
| 19. CX- Wrist Ulnar Deviation |
| 20. CX- Forearm Pronation |
| 21. CX- Forearm Supination |
| 22. HD- Position 1 Hand Grip |
| 23. HD- Position Standard Hand Grip |
| 24. HD- Position 3 Hand Grip |
| 25. HD- Position 4 Hand Grip |
| 26. HD- Position 5 Hand Grip |
| 27. PG- Key Pinch |
| 28. PG- Tip Pinch |
| 29. PG- Palmar Pinch |
| 30. ST- Arm Lift |

FIG. 74A

TABLE 5

| Hip Series Profile: |
| --- |
| 1. Pain Drawing |
| 2. EG- Hip Flexion |
| 3. EG- Hip Extension |
| 4. EG- Hip Internal Rotation |
| 5. EG- Hip External Rotation |
| 6. EG- Hip Abduction |
| 7. EG- Hip Adduction |
| 8. CX- Hip Flexion |
| 9. CX- Hip Extension |
| 10. CX- Hip Abduction |
| 11. CX- Hip Adduction |
| 12. CX- Hip External Rotation |
| 13. CX- Hip Internal Rotation |
| 14. ST- Arm Lift |
| 15. ST- LEG Lift |
| 16. ST- Torso Lift |

FIG. 74B

TABLE 6

| Knee Series Profile: |
| --- |
| 1. Pain Drawing |
| 2. EG- Knee Flexion |
| 3. EG- Knee Extension |
| 4. CX- Hip Flexion |
| 5. CX- Knee Flexion |
| 6. CX- Knee Extension |
| 7. CX- Knee Flexion |
| 8. CX- Hip Extension |
| 9. CX- Hip Abduction |
| 10. CX- Hip Adduction |
| 11. CX- Ankle Inversion |
| 12. CX- Ankle Eversion |
| 13. CX- Ankle Dorsiflexion |
| 14. CX- Ankle Plantar Flexion |
| 15. ST- Arm Lift |
| 16. ST- LEG Lift |
| 17. ST- Floor Lift |

FIG. 74C

TABLE 7

| Elbow Series Profile: |
| --- |
| 1. Pain Drawing |
| 2. EG- Elbow Flexion |
| 3. EG- Elbow Extension |
| 4. EG- Elbow Supination |
| 5. EG- Elbow Pronation |
| 6. CX- Elbow Extension |
| 7. CX- Elbow Extension Elbow Flexed |
| 8. CX- Elbow Flexion Forearm Neutral |
| 9. CX- Elbow Flexion Elbow Pronated |
| 10. CX- Elbow Flexion Elbow Supinated |
| 11. CX- Forearm Pronated |
| 12. CX- Forearm Supinated |
| 13. CX- Wrist Ulnar Deviation |
| 14. CX- Wrist Radial Deviation |
| 15. HD- Position 1 Hand Grip |
| 16. HD- Position Standard Hand Grip |
| 17. HD- Position 3 Hand Grip |
| 18. HD- Position 4 Hand Grip |
| 19. HD- Position 5 Hand Grip |
| 20. PG- Key Pinch |
| 21. PG- Tip Pinch |
| 22. PG- Palmar Pinch |
| 23. ST- Arm Lift |
| 24. ST- High Near |

FIG. 74D

TABLE 8

| Lower Extremity Series Profile: |
| --- |
| 1. Pain Drawing |
| 2. EG- Hip Extension |
| 3. EG- Hip Flexion |
| 4. EG- Hip Internal Rotation |
| 5. EG- Hip External Rotation |
| 6. EG- Knee Flexion |
| 7. EG- Knee Extension |
| 8. EG- Ankle Dorsiflexion |
| 9. EG- Ankle Plantar flexion |
| 10. EG- Ankle Inversion |
| 11. EG- Ankle Eversion |
| 12. CX- Ankle Plantar Flexion |
| 13. CX- Ankle Dorsiflexion |
| 14. CX- Ankle Inversion |
| 15. CX- Ankle Eversion |
| 16. CX- Knee Extension |
| 17. CX- Knee Flexion |
| 18. CX- Hip Adduction |
| 19. CX- Hip Abduction |
| 20. CX- Hip Flexion |
| 21. CX- Hip Internal Rotation |
| 22. CX- Hip External Rotation |
| 23. ST- Torso Lift |
| 24. ST- Floor Lift |
| 25. ST- LEG Lift |

FIG. 74E

TABLE 9

| Lumbar Series Profile: |
| --- |
| 1. Pain Drawing |
| 2. RM- Lumbar Flexion |
| 3. RM- Lumbar Extension |
| 4. RM- Lumbar Lateral Flexion |
| 5. RM- Straight Leg Raise |
| 6. EG- Hip Flexion |
| 7. EG- Hip Extension |
| 8. EG- Knee Flexion |
| 9. EG- Knee Extension |
| 10. CX- Hip Flexion |
| 11. CX- Hip Extension |
| 12. CX- Knee Flexion |
| 13. CX- Knee Extension |
| 14. CX- Ankle Eversion |
| 15. CX- Ankle Inversion |
| 16. CX- Ankle Dorsiflexion |
| 17. CX- Ankle Plantar Flexion |
| 18. ST- Floor Lift |
| 19. ST- Arm Lift |
| 20. ST- LEG Lift |

FIG. 74F

TABLE 10

| Thoracic Series Profile: |
| --- |
| 1. Pain Drawing |
| 2. RM- Thoracic Flexion |
| 3. RM- Thoracic Rotation |
| 4. CX- Scapula Abduction |
| 5. CX- Scapula Adduction |
| 6. CX- Scapula Elevation |
| 7. CX- Scapular Anterior |
| 8. CX- Scapular Posterior |
| 9. HD- Position 1 Hand Grip |
| 10. HD- Position Standard Hand Grip |
| 11. HD- Position 3 Hand Grip |
| 12. HD- Position 4 Hand Grip |
| 13. HD- Position 5 Hand Grip |
| 14. PG- Key Pinch |
| 15. PG- Tip Pinch |
| 16. PG- Palmar Pinch |
| 17. ST- LEG Lift |
| 18. ST- Arm Lift |
| 19. ST- High Near |

FIG. 74G

TABLE 11

| Shoulder Series Profile: |
| --- |
| 1. Pain Drawing |
| 2. EG- Shoulder Flexion |
| 3. EG- Shoulder Extension |
| 4. EG- Shoulder Abduction |
| 5. EG- Shoulder Adduction |
| 6. EG- Shoulder External Rotation |
| 7. EG- Shoulder Internal Rotation |
| 8. CX- Shoulder Flexion |
| 9. CX- Shoulder Extension |
| 10. CX- Shoulder Abduction |
| 11. CX- Shoulder Adduction |
| 12. CX- Shoulder External Rotation |
| 13. CX- Shoulder Internal Rotation |
| 14. HD- Position 1 Hand Grip |
| 15. HD- Position Standard Hand Grip |
| 16. HD- Position 3 Hand Grip |
| 17. HD- Position 4 Hand Grip |
| 18. HD- Position 5 Hand Grip |
| 19. PG- Key Pinch |
| 20. PG- Tip Pinch |
| 21. PG- Palmar Pinch |
| 22. ST- Arm Lift |
| 23. ST- High Near |
| 24. ST- High Far |

FIG. 74H

TABLE 12

| Upper Extremity Series Profile: |
| --- |
| 1. Pain Chart |
| 2. EG- Shoulder Flexion |
| 3. EG- Shoulder Extension |
| 4. EG- Shoulder Abduction |
| 5. EG- Shoulder Adduction |
| 6. EG- Elbow Flexion |
| 7. EG- Elbow Extension |
| 8. EG- Wrist Dorsiflexion |
| 9. EG- Palmar Flexion |
| 10. CX- Shoulder Flexion |
| 11. CX- Shoulder Extension |
| 12. CX- Shoulder Abduction |
| 13. CX- Shoulder Adduction |
| 14. CX- Elbow Extension |
| 15. CX- Elbow Flexion |
| 16. CX- Wrist Dorsiflexion |
| 17. CX- Wrist Palmar Flexion |
| 18. HD- Position 1 Hand Grip |
| 19. HD- Position Standard Hand Grip |
| 20. HD- Position 3 Hand Grip |
| 21. HD- Position 4 Hand Grip |
| 22. HD- Position 5 Hand Grip |
| 23. PG- Key Pinch |
| 24. PG- Tip Pinch |
| 25. PG- Palmar Pinch |
| 26. ST- Arm Lift |
| 27. ST- High Far Lift |
| 28. ST-High Near Lift |

FIG. 74I

TABLE 13

| Mua Series Profile: |
| --- |
| 1. RM- Cervical Flexion |
| 2. RM- Cervical Extension |
| 3. RM- Cervical Lateral Flexion |
| 4. RM- Cervical Rotation |
| 5. RM- Lumbar Flexion |
| 6. RM- Lumbar Extension |
| 7. RM- Lumbar Lateral Flexion |
| 8. RM- Thoracic Flexion |
| 9. RM- Thoracic Extension |
| 10. EG- Shoulder Flexion |
| 11. EG- Shoulder Extension |
| 12. EG- Shoulder Abduction |
| 13. EG- Shoulder Internal Rotation |
| 14. EG- Shoulder External Rotation |
| 15. EG- Hip Flexion |
| 16. EG- Hip Extension |
| 17. EG- Hip Internal Rotation |
| 18. EG- Hip External Rotation |
| 19. EG- Hip Abduction |
| 20. EG- Hip Adduction |
| 21. CX- Elbow Flexion |
| 22. CX- Elbow Extension |
| 23. CX- Cervical Flexion |
| 24. CX- Cervical Extension |
| 25. CX- Cervical Lateral Flex |
| 26. CX- Scapula Anterior |
| 27. CX- Scapula Posterior |
| 28. CX- Scapular Abduction |
| 29. CX- Scapular Adduction |
| 30. CX- Shoulder Flexion |
| 31. CX- Shoulder Extension |
| 32. CX- Shoulder Abduction |
| 33. CX- Shoulder External Rotation |
| 34. CX- Shoulder Internal Rotation |
| 35. CX- Hip Flexion |
| 36. CX- Hip Extension |
| 37. CX- Hip Internal Rotation |
| 38. CX- Hip External Rotation |
| 39. CX- Hip Abduction |

FIG. 74J

TABLE 14

| Functional Screening Series Profile: |
| --- |
| 1. RM- Cervical Flexion |
| 2. RM- Cervical Extension |
| 3. RM- Cervical Lateral Flexion |
| 4. RM- Cervical Rotation |
| 5. RM- Lumbar Flexion |
| 6. RM- Lumbar Extension |
| 7. RM- Lumbar Lateral Flexion |
| 8. RM- Straight Leg Raise |
| 9. EG- Hip Flexion |
| 10. EG- Hip Extension |
| 11. EG - Shoulder Flexion |
| 12. EG - Shoulder Extension |
| 13. EG - Shoulder Abduction |
| 14. EG - Shoulder External Rotation |
| 15. EG - Shoulder Internal Rotation |
| 16. CX- Elbow Flexion |
| 17. CX- Elbow Extension |
| 18. CX- Cervical Flexion |
| 19. CX- Cervical Extension |
| 20. CX- Cervical Lateral Flex |
| 21. CX- Shoulder Flexion |
| 22. CX- Shoulder Extension |
| 23. CX- Shoulder Abduction |
| 24. CX- Shoulder External Rotation |
| 25. CX- Shoulder Internal Rotation |
| 26. CX- Hip Flexion |
| 27. CX- Hip Extension |
| 28. CX- Hip Internal Rotation |
| 29. CX- Hip External Rotation |
| 30. CX- Hip Abduction |
| 31. HD- Position Standard Hand Grip |
| 32. PG- Key Pinch |
| 33. PG- Tip Pinch |
| 34. PG- Palmar Pinch |
| 35. ST- Arm Lift |
| 36. ST- LEG Lift |

FIG. 74K

COMPUTER-AIDED MULTIPLE STANDARD-BASED FUNCTIONAL EVALUATION AND MEDICAL REPORTING SYSTEM

CROSS REFERENCES TO RELATED APPLICATIONS

This application claims priority on U.S. application Ser. No. 12/804,646, filed on Jul. 26, 2010, the disclosures of which are incorporated herein by reference.

FIELD OF THE INVENTION

The present invention relates to improvements in making a determination of a patient's functional ability and treatment effectiveness, and more particularly to a means of providing computer-linked test-specific hardware utilized in combination with test-specific protocols.

BACKGROUND OF THE INVENTION

There are basically six different types of medical tests which may be performed on a patient, and for various reasons, using specialized equipment, including: analysis of bodily fluids (blood, urine, spinal cord & brain-cerebrospinal fluid, joint fluid-synovial fluid); imaging (x-rays, ultrasonogaphy, radioisotope scanning, computed tomography—CT, magnetic resonance imaging—MRI, positron emission tomography-PET, and angiography); endoscopy (nose, mouth, anus, urethra, and vagina); tissue biopsy (skin, breast, lung, liver, kidney, and bone); genetic testing; and measurement of bodily functions (brain-electroencephalography or EEO, heart-electrocardiography or ECG, and muscle strength and range or motion).

The measurement of bodily function, particularly with regard to physical impairment, plays an important and intertwined role between the medical community—as to diagnosis, treatment, and treatment affectivity—and the legal community—as to liability and damages. A person's level of impairment is significant for tort liability due to automobile and other accidents, and also as to on-the-job work-related accidents, which are governed by state and federal Worker's Compensation Law, and Social Security disability claims. A list of impairments that Congress has determined to be disabling are found in the disability handbook, which is called Disability Evaluation under Social Security, or more commonly known as the Blue Book. The handbook, which may be found electronically at socialsecurity.gov, lists the categories of impairments, which include impairment of the musculoskeletal system.

The Social Security Administration (SSA) defines a medically determinable impairment as "an impairment that results from anatomical, physiological, or psychological abnormalities which can be shown by medically acceptable clinical and laboratory diagnostic techniques." But, the Social Security rules create a system where a person is either entirely disabled or not disabled at all. However, rating the degree of impairment is essential in workers compensation cases. According to the fifth edition of the "Guides to the Evaluation of Permanent Impairment," published by the American Medical Association (AMA), impairment is defined as "an alteration of an individual's health status; a deviation from normal in a body part or organ system and its functioning." The AMA Guides also hold that impairments that are to be rated are permanent impairments, meaning one that has reached maximum medical improvement (MMI) and is well stabilized and unlikely to change substantially in the next year with or without medical treatment.

Although individual state law governing workers' compensation provides its own unique definition of impairment, they are generally consistent with the definition found in the AMA Guides. In fact, while about fourteen states either use state-specific guidelines or do not specify a specific guideline, some thirty-six states use the AMA Guides $2^{nd}$, $3^{rd}$, $4^{th}$, $5^{th}$, and $6^{th}$ editions. The fifth edition is currently the most popular, seeing usage by sixteen states. Therefore, a person's physical impairment rating is a critical factor in many states.

To appropriately adjudicate a claim, it is essential to use a functional evaluation that provides an accurate and unbiased clinical understanding of a person's true physical ability. Without this objective information, inappropriate claim decisions can result in increased lost time, unnecessary treatment and the opportunity to abuse the claims process. This is unacceptable for all parties who expect an equitable resolution of a claim.

This invention makes use of protocols to standardize a process and a computer program. Such an approach within the medical community is, by itself, not new. The use of protocols was demonstrated in related art shown by U.S. Pat. No. 5,833,623 to Mann for "System and Method for Facilitating Rapid Retrieval and Evaluation of Diagnostic Data Stored by an Implantable Medical Device," and U.S. Pat. No. 5,873,894 to Vandegriff for "Diagnostic Test Protocol in an Implantable Medical Device." The former records diagnostic heart data for later retrieval and evaluation, not unlike systems used for recording seismic data. The latter arrangement provides for communication between the medical device and the programmer, including an output signal to transmit information on the status of the medical device. But both inventions are narrowly focused on heart pacemaker activity and other devices similarly implanted in the human body.

In U.S. Pat. No. 6,827,670 to Stark for "System for Medical Protocol Management," the invention is targeted at providing an appropriate orthopedic treatment protocol with modification of the treatment based on feedback data recorded by a computerized orthopedic treatment device, and analyzed by an interaction algorithm. However, the analysis is based on orthopedic treatment protocols, using challenge levels associated with an injury, but does not specify the evaluation means or the standards used for evaluating functional abilities.

However, the invention disclosed herein is a unique merger of resources to obtain synergy specifically directed at producing repeatable, consistent impairment ratings, through use of a specialized functional evaluation. The resources comprise: a range of selectable standards for evaluation, including the different editions of the AMA guides; a computer program particularly designed to amass empirical test data in accordance with the standard selected; a wide variety of evaluation protocols, and testing tools, many of which have been modified to input data directly into the computer diagnostic program, in addition to the option of making manual entries; and automatic report generation.

OBJECTS OF THE INVENTION

It is an object of the invention to provide a means of conducting a repeatable functional evaluation of a patient's ability.

It is another object of the invention to provide a functional evaluation utilizing software to repeatably and accurately calculate impairment ratings.

It is a further object of the invention to provide a means of assessing an impairment rating for use in work-related injury claims.

It is another object of the invention to provide a means of assessing impairment based on each edition of the AMA Guides to the Evaluation of Permanent Impairment.

It is also an object of the invention to provide a means of assessing impairment that correlates to the nursing standard found in the Activities of Daily Living.

It is another object of the invention to provide a means of assessing impairment based on sports medicine frames of reference.

SUMMARY OF THE INVENTION

A method of performing an objective functional evaluation of a person's physical ability is incorporated in a software program which utilizes specialized testing instruments. The instruments are used to measure distinct physical capabilities of a person, by using the equipment in multiple trials of a condition-specific protocol of tests. The tests may be selected from a pictorial image on a computer screen according to symptoms exhibited by the patient, or they may be selected directly from a pull-down menu of test. The system permits calibration of the equipment, which may be offered in a transportable arrangement to allow mobile evaluations by a single person.

Data entry of the measurements into an algorithm within the software program may be direct, through a wireless or a wired interface to the computer system. The algorithm may calculate a coefficient of variation for the multiple trials using the entered data. A second algorithm may calculate an average result of the measurements of the condition-specific protocol of tests, which may be correlated to a database of normative standards to compute an impairment rating. The coefficient of variation comprises a difference that is computed as a percentage between measurements in successive trials. When the calculated coefficient of variation for three successive trials is approximately 15% or less, the trial results are valid, reproducibility, and demonstrate consistency of effort. If three successive trials do not fall within the acceptable range, a fourth, fifth, and sixth trial may be performed to achieve validity.

If validity is not achieved within the six trials, then the entire test is invalid. The average results are arranged in an easily scannable format that accommodates ready identification by a doctor of functional loss, and may be retained in individual patient records. The format may comprise a table of the average results and normative standards, or it may comprises a color coded bar chart of the average results and normative standards. The software contains instruction to generate on-screen display of the easily scannable results, or a comprehensive printable report. The coefficient of variation may be tied to the various editions of the AMA's "Guides To The Evaluation of Permanent Impairment."

The condition-specific protocol of tests may include: an ankle/foot series profile, a cervical series profile, a cervical/elbow series profile, a cervical/wrist series profile, a carpal tunnel series profile, a hip series profile, a knee series profile, an elbow series profile, a lower extremity series profile, a lumbar series profile, a thoracic series profile, a shoulder series profile, an upper extremity series profile, or a functional screening series profile.

The system serves to quantify muscle weakness and loss of range of motion to objectively identify when a person is misrepresenting their true physical ability. It also permits identification of nerve injuries, quantifies rehabilitation improvement, provides legally defensible documentation for litigation, establishes medical necessity for treatment, tracks patient progress during stages of care, and identifies whole-person impairment and regional impairment.

BRIEF DESCRIPTION OF THE DRAWINGS

FIG. 15 illustrates the utility screen of FIG. 14 asking for the goniometer to be set to 0° by closing the arms all the way together, before clicking the "OK" Button on the screen.

FIG. 18 illustrates the calibration process of FIG. 14, but for 90 degrees.

FIG. 38 illustrates the additional button bar buttons added after the patient button is clicked.

FIG. 39 highlights the "new patient" button of FIG. 38.

FIG. 40 highlights the patient record screen portion of the patient database window of FIG. 37.

FIG. 73A, TABLE 1. is a chart listing the reasons for performing each of the thirteen protocols of FIG. 73.

FIG. 73B, TABLE 2, lists the tests performed in an Ankle Series Profile for a functional evaluation.

FIG. 73C, TABLE 3, lists the tests performed in a Cervical Series Profile for a functional evaluation.

FIG. 74 illustrates the first six tests performed in the Cervical Series Profile of FIG. 114.

FIG. 74A, TABLE 4, lists the tests performed in a Carpal Tunnel Series Profile for a functional evaluation.

FIG. 74B, TABLE 5, lists the tests performed in a Hip Series Profile for a functional evaluation.

FIG. 74C, TABLE 6, lists the tests performed in a Knee Series Profile for a functional evaluation.

FIG. 74D, TABLE 7, lists the tests performed in an Elbow Series Profile for a functional evaluation.

FIG. 74E, TABLE 8, lists the tests performed in a Lower Extremity Series Profile for a functional evaluation.

FIG. 74F, TABLE 9, lists the tests performed in a Lumbar Series Profile for a functional evaluation.

FIG. 74G, TABLE 10, lists the tests performed in a Thoracic Series Profile for a functional evaluation.

FIG. 74H, TABLE 11, lists the tests performed in a Shoulder Series Profile for a functional evaluation.

FIG. 74I, TABLE 12, lists the tests performed in an Upper Extremity Series Profile for a functional evaluation.

FIG. 74J. TABLE 13, lists the tests performed in a MUA Series Profile for a functional evaluation.

FIG. 74K, TABLE 14, lists the tests performed in a Functional Screening Series Profile.

DETAILED DESCRIPTION OF THE INVENTION

Figure 1:
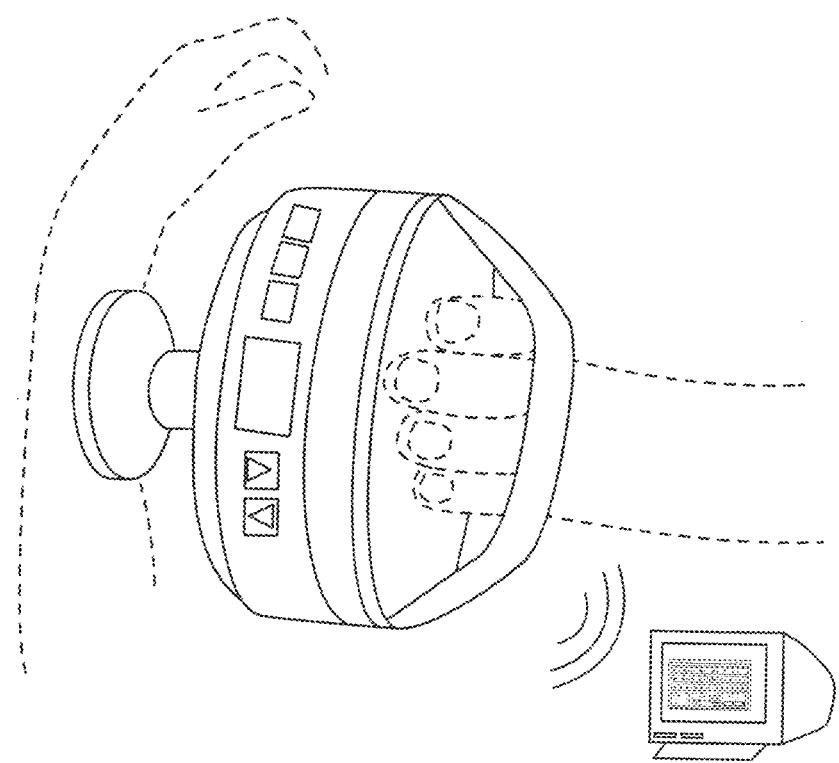
FIG. 1 is a photograph of a wireless version of a muscle tester used to input data directly into a computer running the software program of the present invention.

A Functional Evaluation that is based on qualitative observation is not inherently an evaluation process. Since there is no measurement system, there can be no evaluation arising from professional judgment. In the past, an assessment of impairment was highly subjective. Today, the American Medical Association's Guides to the Evaluation of Permanent Impairment, and other standard-based systems, provide a means for making a determination as to impairment with a numerical rating in terms of a percentage.

The system of the present invention provides an objective computerized functional evaluation and reporting system. Such an evaluation may serve many purposes, in addition to providing an impairment rating, including, but not limited to: providing objective documentation for insurance carriers; quantifying muscle weakness and loss of range of motion; identifying nerve injuries; locating functional deficits; quantifying rehabilitation improvement; providing a detailed whole body pain chart; providing legally defensible documentation for litigation; establishing medical necessity for treatment; increasing patient retention for doctors, tracking patient progress, determining whole person impairment or regional impairment; and assessing ability in terms of activities of daily living. The system of the present invention has three key components-, a standard-based computer program tailored for performing a functional evaluation. various pieces of testing hardware that may include a hardware/software interface, and an advanced reporting capability. Together these components create a powerful evaluation tool that allows users to perform objective functional evaluations.

A complete set testing of equipment may be obtained from Medsourceva, which is located at 5251-18 John Tyler Hwy #242, in Williamsburg, Va. 23185. The testing equipment that can be used in the process may include, but is not limited to, a hand dynamometer, a pinch gauge, range of motion inclinometers, an electronic goniometer, a heart rate monitoring system, a pressure algometer, a dynamic/static lifting platform, push/pull carts, and a dexterity cube. Many of the pieces of equipment used in conjunction with the software of the current invention may employ wireless technology to transmit testing data directly to the computer system running the software, in order to efficiently collect and analyze the data. One example is shown by the wireless pressure algometer 100 of FIG. 1. Many other pieces of equipment may alternatively have a cable connection to a port on a peripheral that is linked to the computer. The program running on the computer system may accept manual entry, by the operator, of the results of such tests. For a better understanding of the invention herein, a description of an exemplary computer system is disclosed, and may be found at the end of the specification.

As stated previously, the method described herein will utilize many pieces of specialized test equipment in conjunction with the specially developed computer software program, running on computer system, to guide an operator through the appropriate test sequence. The software program may cause one or more specific windows to appear on the computer system's monitor or LCD screen. Each of the windows may prompt the operator to perform steps in the evaluation.

Figure 2:
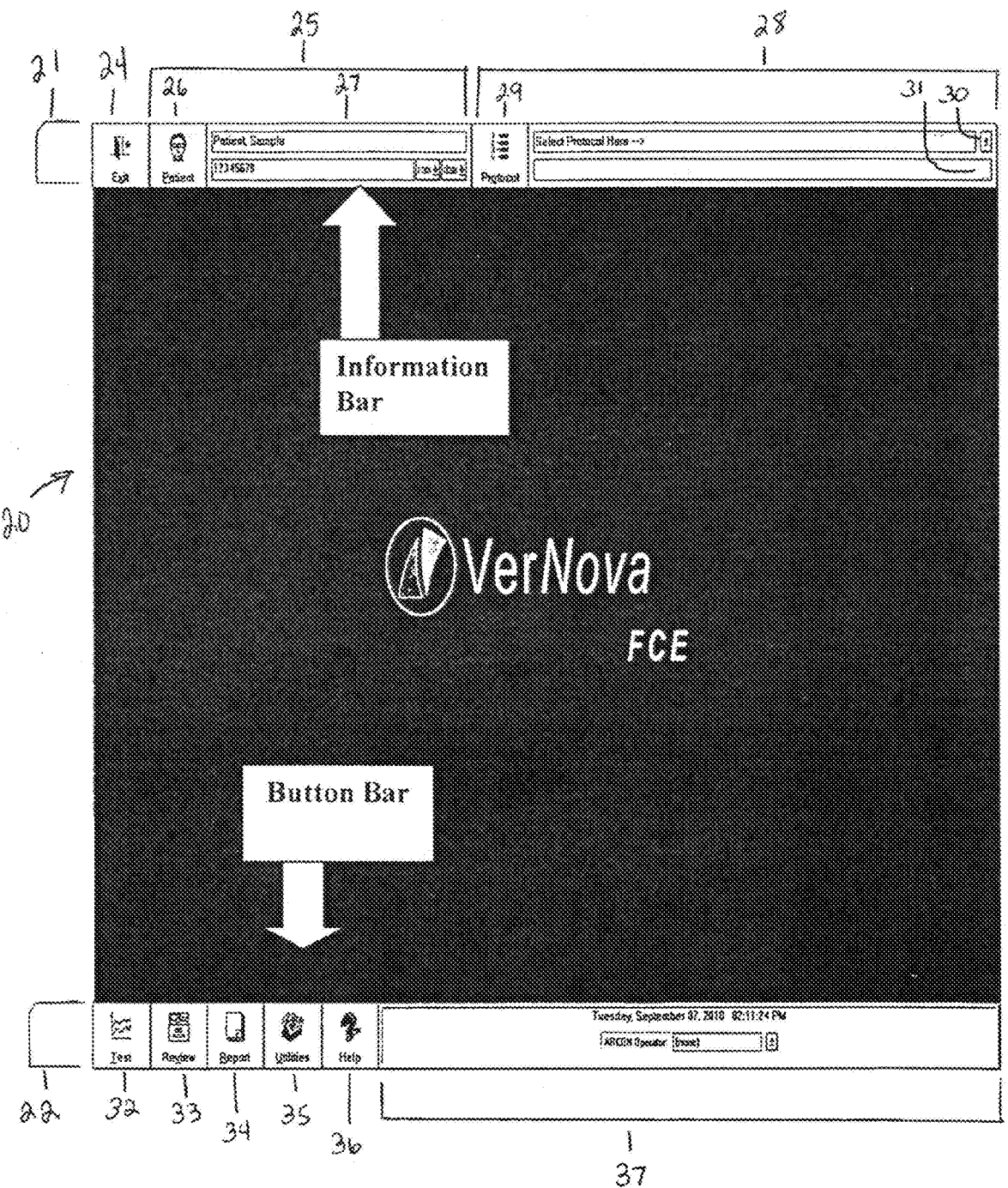
FIG. 2 illustrates the Software Main Screen Overview.

When properly loaded into and running on a computer system 11, such as the one shown in FIG. 1, the software will cause the main window 20 shown in FIG. 2 to appear on the computer monitor. The main window 20 may be comprised of an "information bar" 21 at the top of the window, and a "button bar" 22 at the bottom of the window. The information bar 21 may be comprised of an exit button 24 for closing the software, a patient panel 25, which may be comprised of a patient button 26, a current patient name/I.D. # window 27, and a protocol panel 28, which may be comprised of a protocol button 29, a current protocol window 30, and a current test window, each of which will be discussed later in more detail. The button bar 22 may initially be comprised of test button 32, a review button 33, a report button 34, a utilities button 35, a help button 36, and an operator drop-down window 37. Each of the buttons may best be understood in discussing the method herein.

Figure 3:
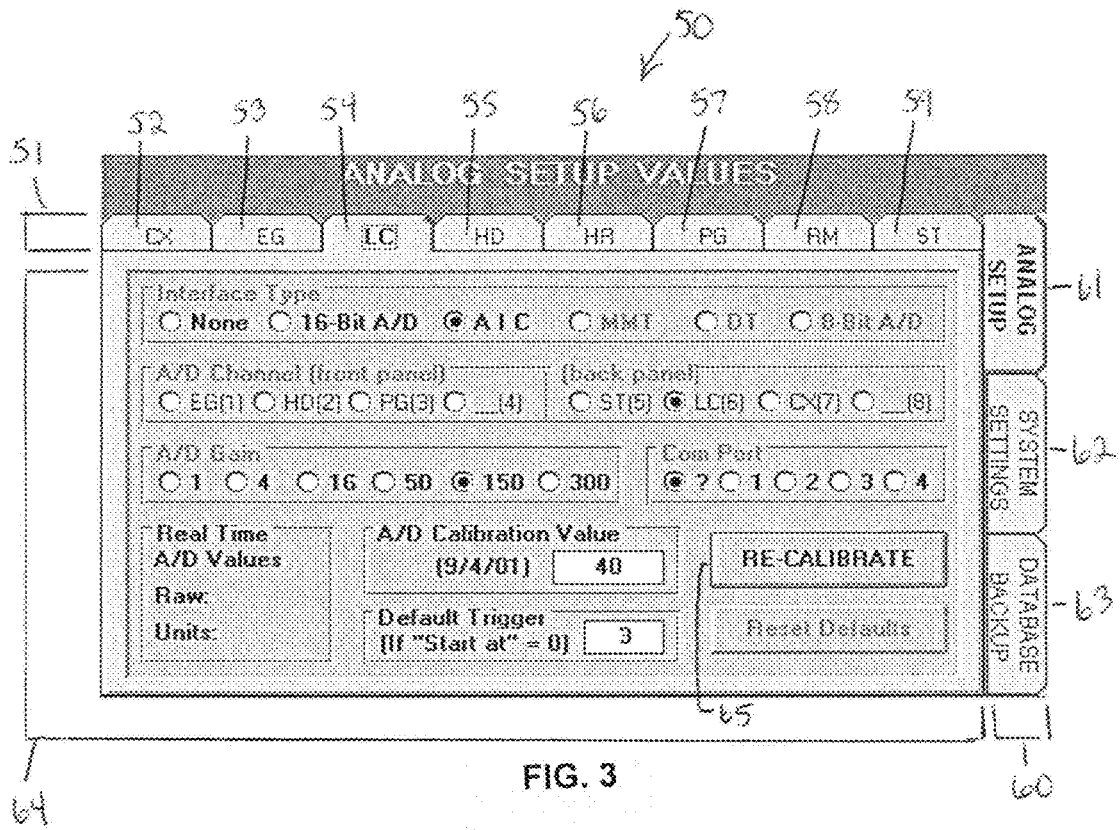
FIG. 3 illustrates the utilities screen which contains a number of utility option tabs down the side of the screen, with the Analog Setup default option being used for calibration of equipment listed by the tabs across the top of the screen.

A first place to begin when performing a functional evaluation in accordance with the method of the current invention is to calibrate the equipment and/or perform an equipment check to ensure its proper functioning. Equipment calibration should be performed once a month with normal use, and once a week with frequent or rough use. Equipment calibration may be performed using the utilities screen 50 shown in FIG. 3, which may be launched using the utilities button 35 of the software main window 20.

The utilities screen 50 contains a number of "index tabs" 51 across the top of the screen. The index tabs 51 are for the different testing instruments accommodated by the software, and include the CX tab 51, EG tab 52, LC tab 54, HD tab 55, HR tab 56, PG tab 57, RM tab 58, and the ST tab 59. Each instrument tab contains the setup values used to read that instrument on the custom Analog-to-Digital Converter supplied with the system. The "option" tabs 60 down the side of the utilities screen 50 are used to select different utility options, and include the analog setup tab 61, the system settings tab 62, and the database backup tab 63. The analog setup tab 61 is the default option, and is used for equipment calibration. It will display the instrument tabs when selected.

Figure 4:
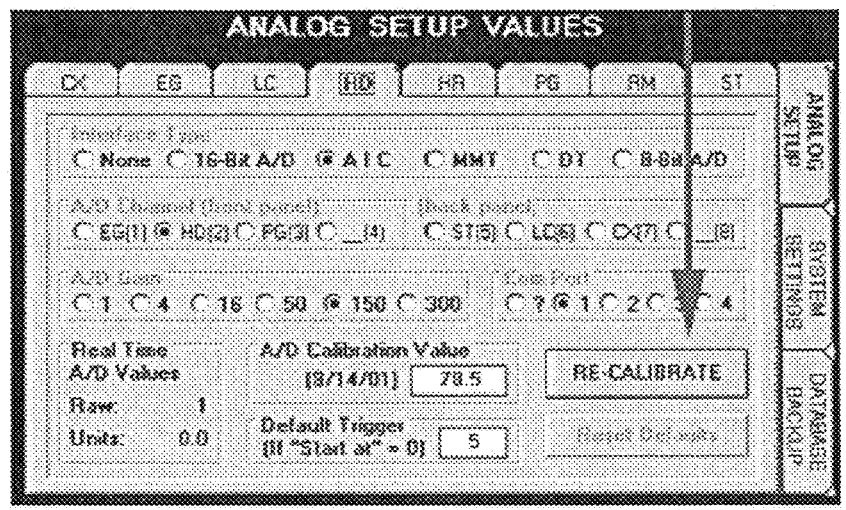
FIG. 4 illustrates the HD Tab on the Utility Screen of FIG. 3 used to Re-Calibrate the hand dynamometer.
Figure 5:
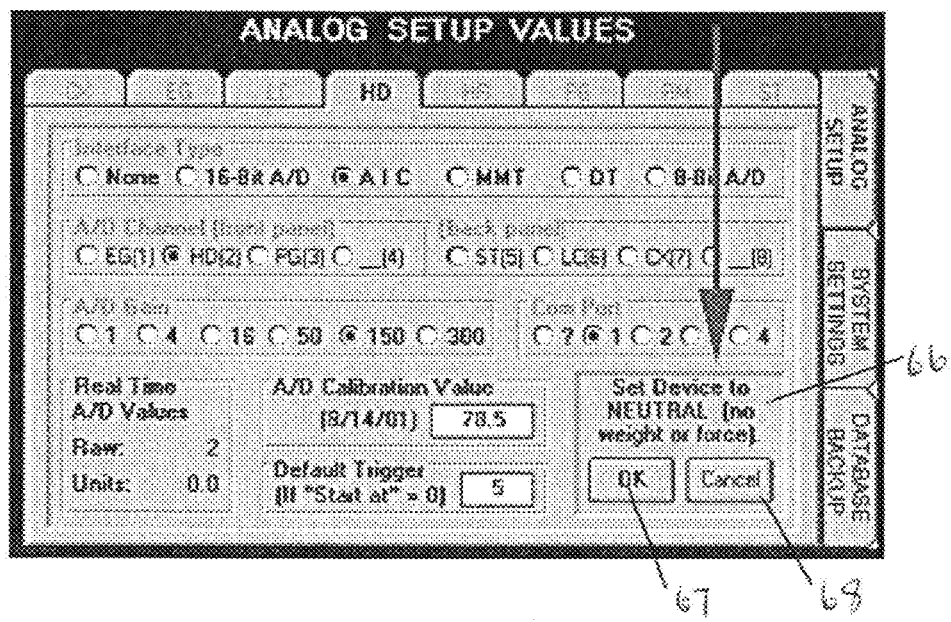
FIG. 5 illustrates the next instructional step on the Utility Screen for re-calibrating the hand dynamometer.
Figure 6:
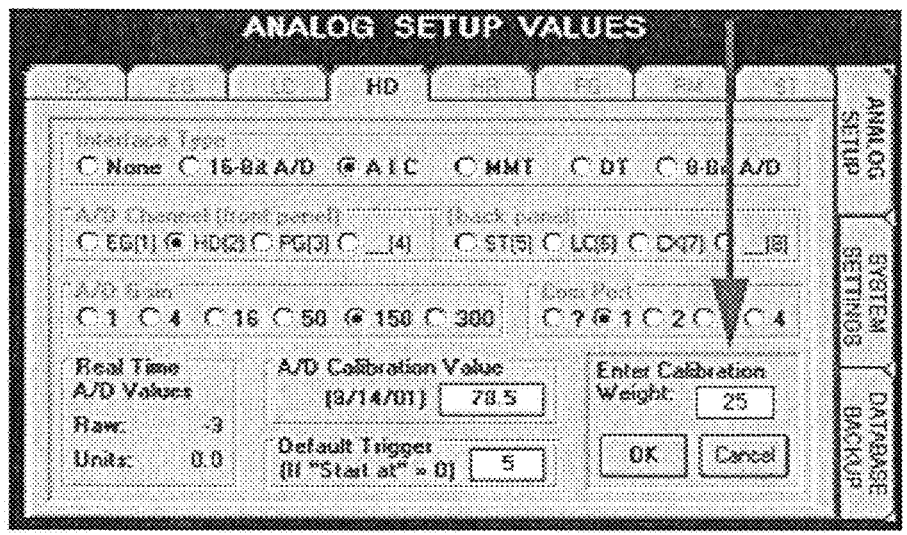
FIG. 6 illustrates the window on the utilities screen into which is to be entered the value of the calibration weight loaded onto the hand dynamometer.
Figure 7:
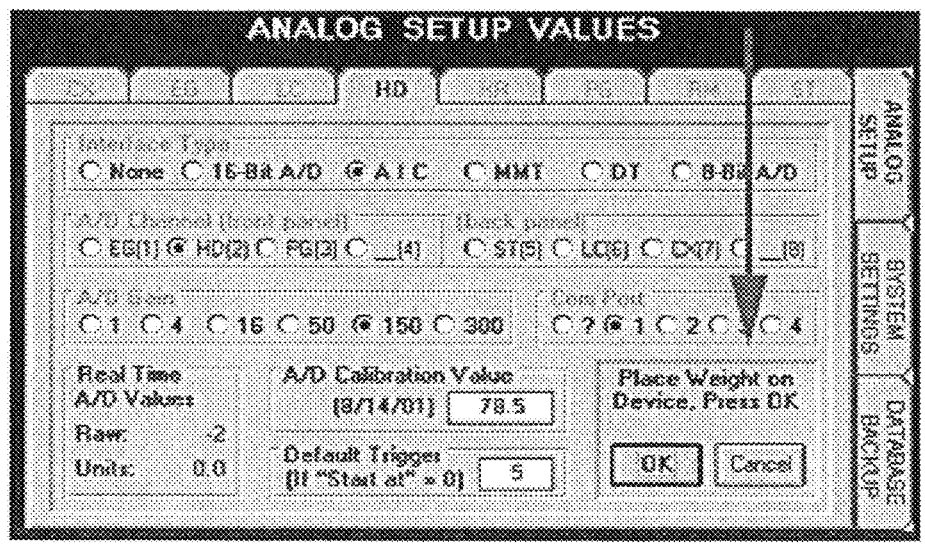
FIG. 7 illustrates the window on the utilities screen instructing the user to click ok, once the weight is atop the hand dynamometer.

The calibration process for each piece of equipment is similar, and may proceed by selecting the appropriate tab in the utilities window 50, as seen in FIG. 4. To calibrate the hand dynamometer, the user would select the HD tab 55 of the utilities window 50, and then click on the "re-calibrate" button 65. The re-calibrate button 65 will then be replaced by a message area 66 that also has an "OK" button 67 and a "cancel button 68. The message area will say "set device to neutral," meaning that it should be positioned in a calibration jig. Once properly positioned, the OK button 67 can be clicked on using a mouse or other pointing device. The message area 66 will then say "enter calibration weight" beside a new window 69 where the weight value may be entered (FIG. 6).

Figure 8:
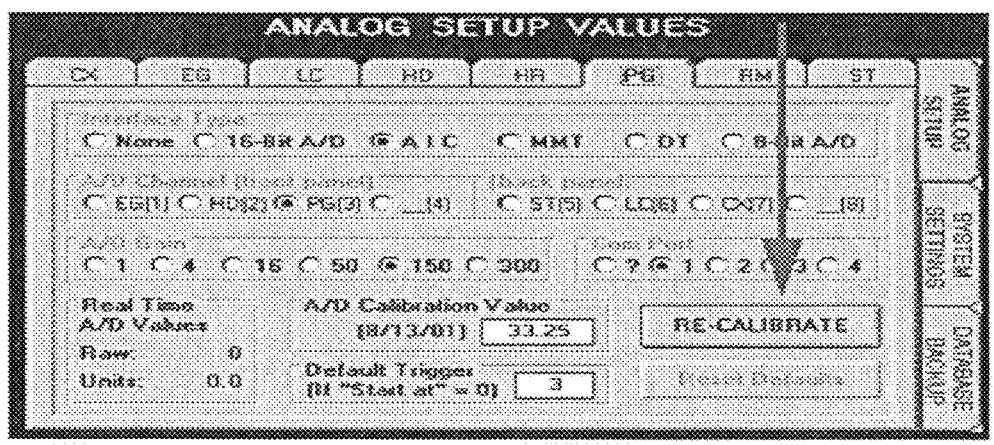
FIG. 8 illustrates the PG Tab on the Utility Screen of FIG. 3 used to Re-Calibrate the pinch gauge.
Figure 9:
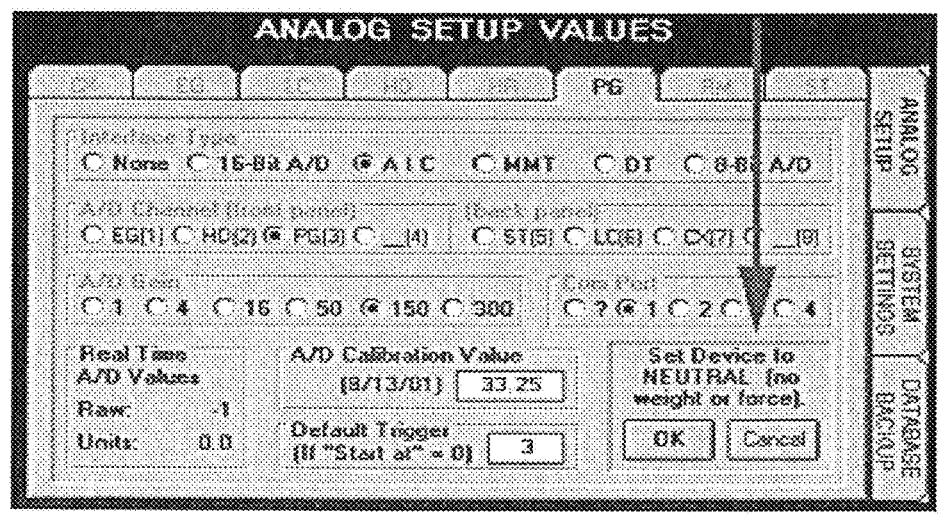
FIG. 9 illustrates the next instructional step on the Utility Screen for re-calibrating the pinch gauge.
Figure 10:
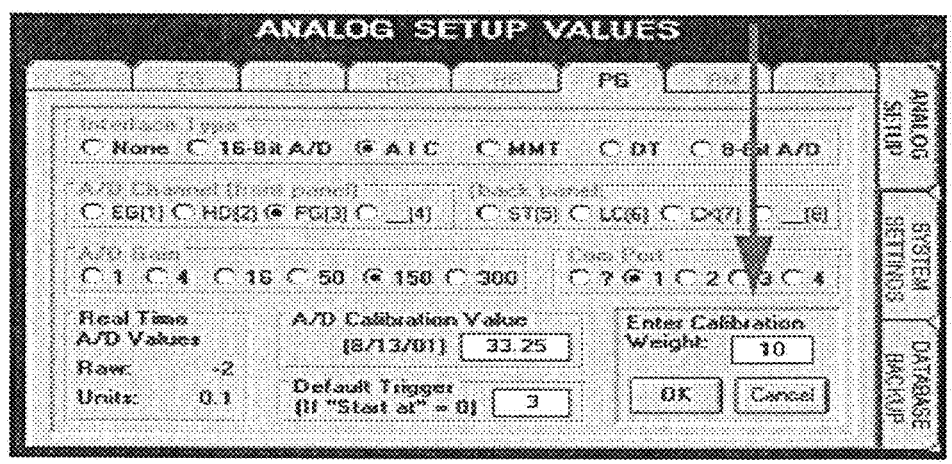
FIG. 10 illustrates the window on the utilities screen into which is to be entered the value of the calibration weight loaded onto the pinch gauge.
Figure 11:
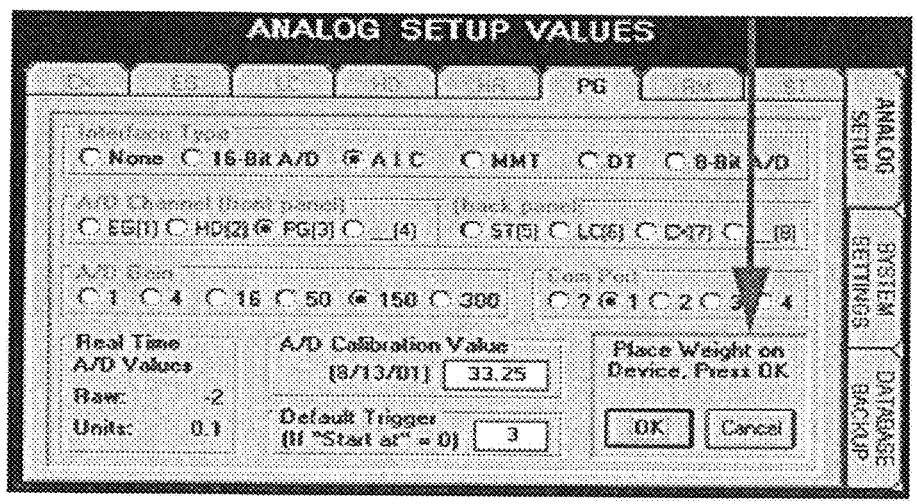
FIG. 11 illustrates the window on the utilities screen instructing the user to click ok. once the weight is atop the pinch gauge.
Figure 12:
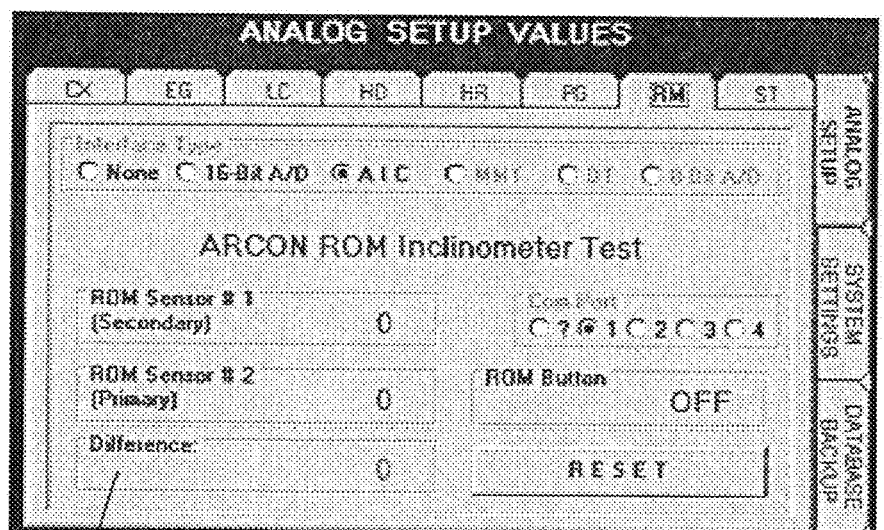
FIG. 12 illustrates the RM Tab on the Utility Screen of FIG. 3 being used to check proper functioning of the dual inclinometers.

It is recommended that at least a 20 pound weight be used for calibration. The weight used should also be a known weight, meaning that it is a certified weight or you have verified its weight on a reliable or a calibrated scale. This calibration weight should be entered in the field, with the user then clicking the "OK" 67 Button. The message area 66 now states "place weight on device, press OK." Once the weight is placed on the HD and the "OK" button has been thereafter clicked, the weight that was placed on the hand dynamometer will match the unit value within a couple tenths, and the HD will then be calibrated. Calibration of the pinch gauge is accomplished using the PG tab 57 (FIG. 8), and follows the same process as for the HD. The range of motion (ROM or RM) dual inclinometers do not calibrate, but can be tested in order to be certain that they are functioning correctly using the RM Tab 58 on the utility screen 50.

Figure 13:
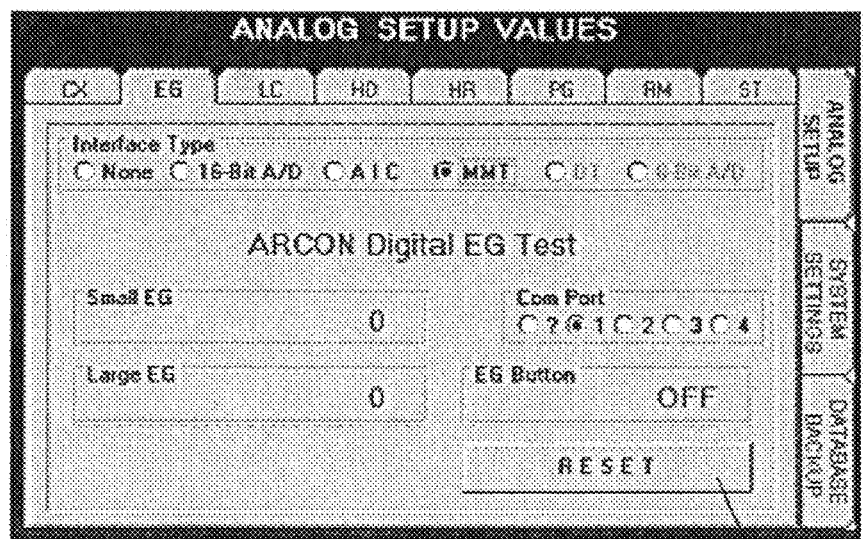
FIG. 13 illustrates the EG Tab on the Utility Screen of FIG. 3 being used to check proper functioning of the digital goniometer set.
Figure 14:
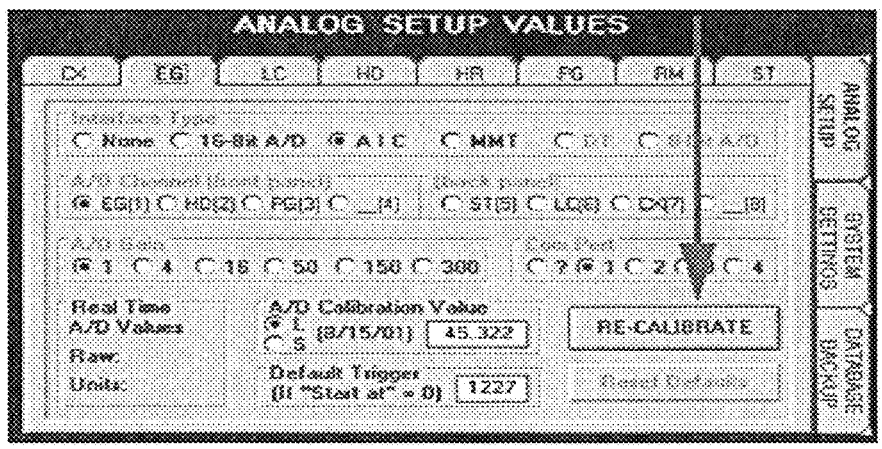
FIG. 14 illustrates the EG Tab on the Utility Screen of FIG. 3 being used to calibrate either the small or large analog goniometer set.
Figure 16:
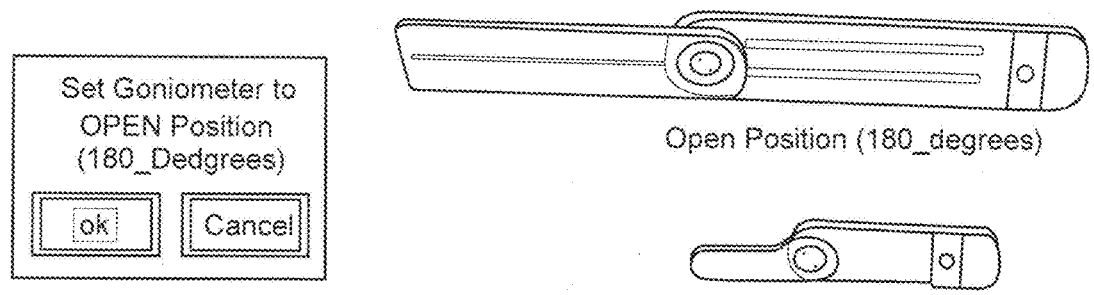
FIG. 16 illustrates the calibration process of FIG. 14, but for 180 degrees.
Figure 17:
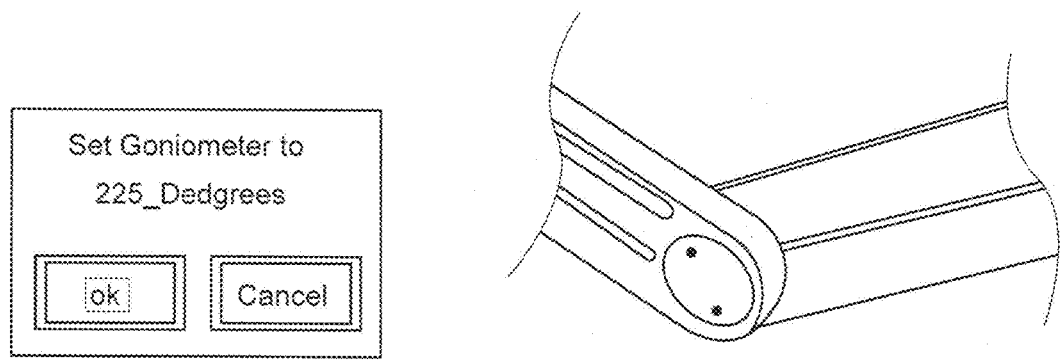
FIG. 17 illustrates the calibration process of FIG. 14, but for 225 degrees.
Figure 19:
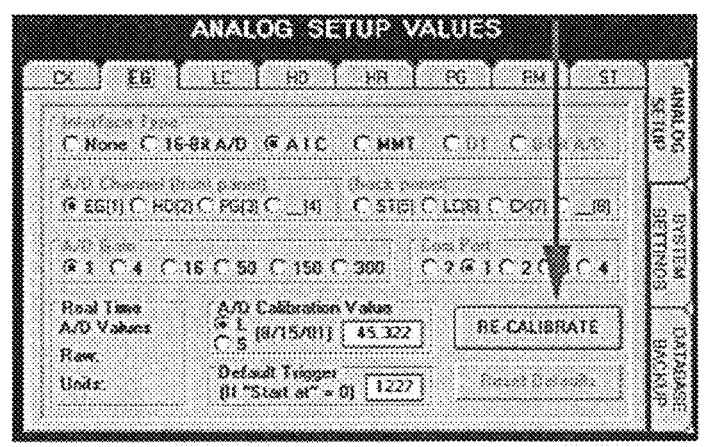
FIG. 19 illustrates the EG Tab on the Utility Screen of FIG. 6 being used to calibrate the older single goniometer.
Figure 20:
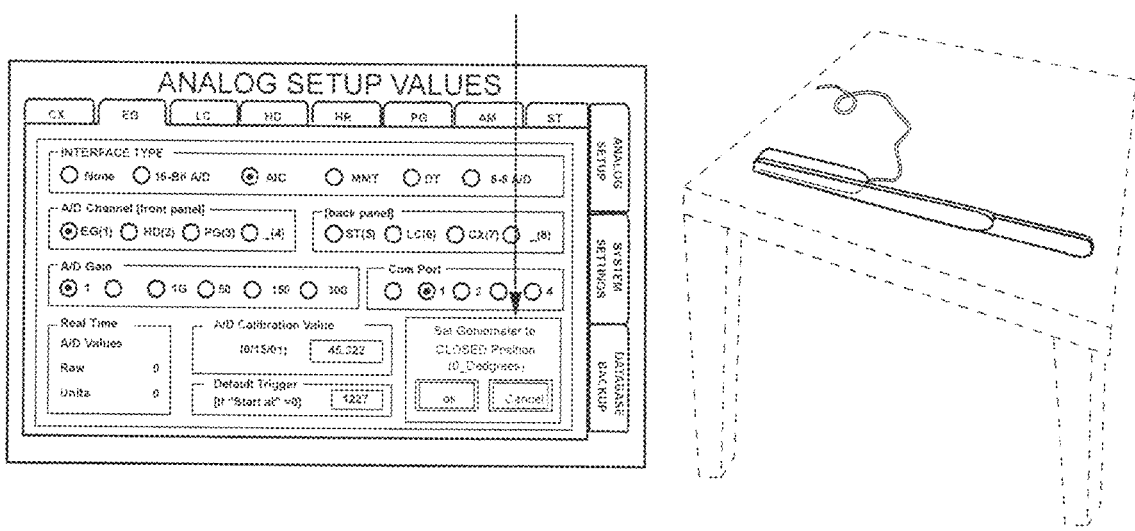
FIG. 20 illustrates the 0 degree alignment and utility screen setting used to calibrate the older single goniometer.
Figure 21:
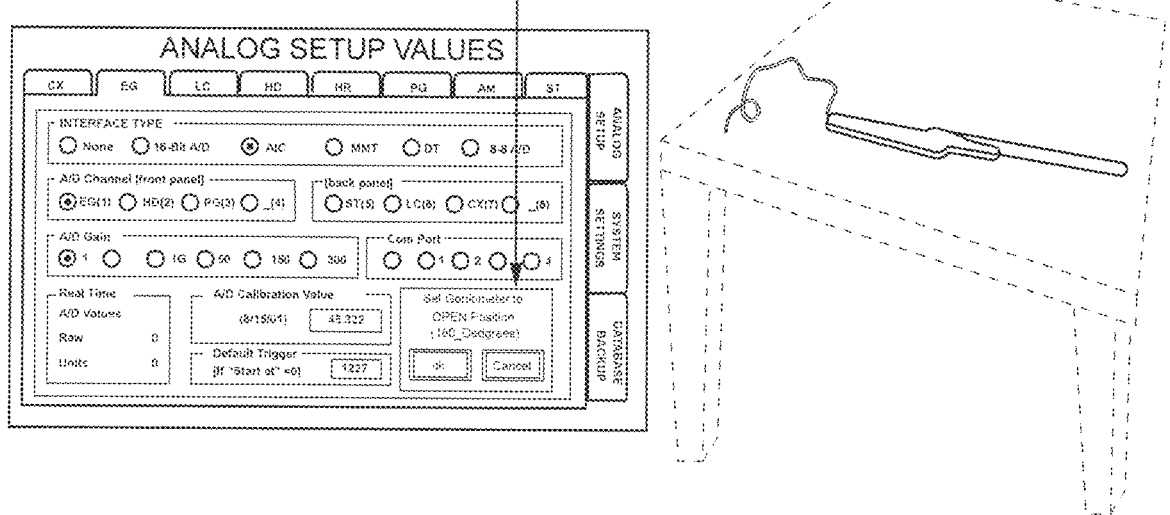
FIG. 21 illustrates the 180 degree alignment and utility screen setting used to calibrate the older single goniometer.
Figure 22:
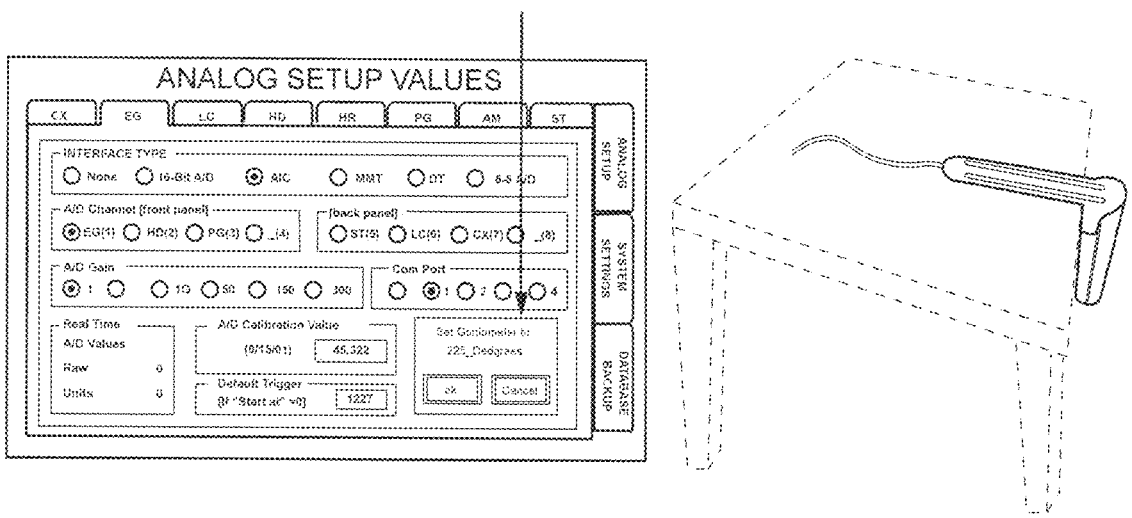
FIG. 22 illustrates the 90 degree alignment and utility screen setting used to calibrate the older single goniometer.
Figure 23:
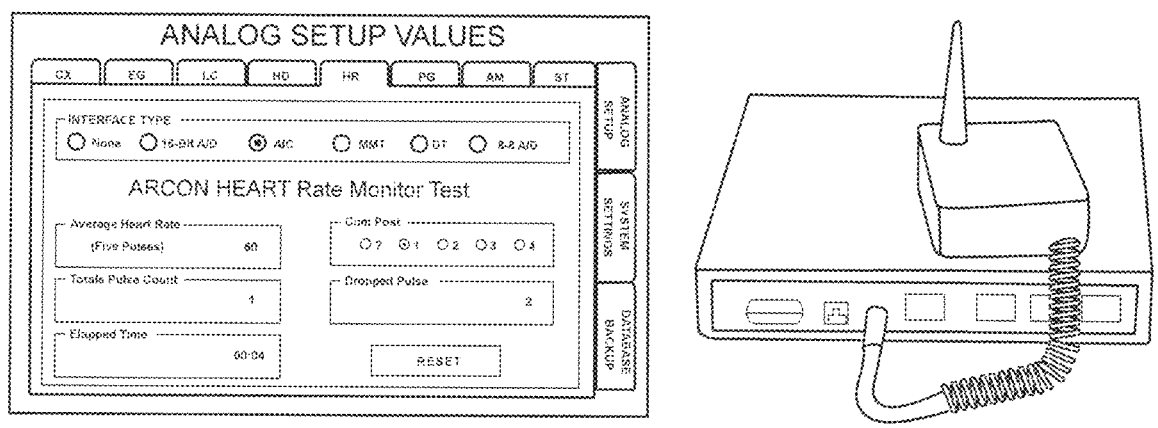
FIG. 23 illustrates the utility screen used for testing of proper functioning of the extended heart rate monitor.
Figure 24:
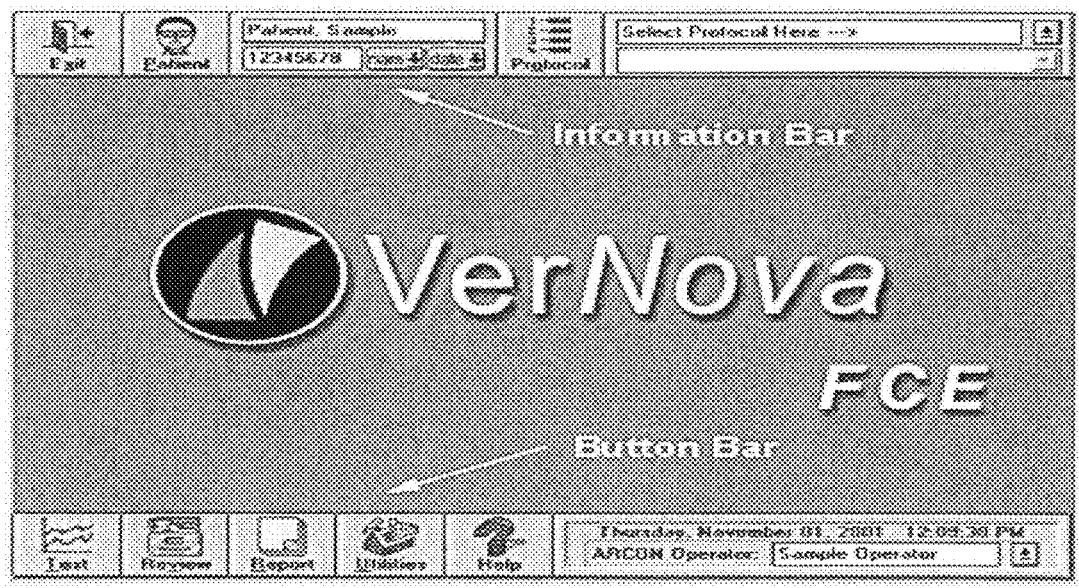
FIG. 24 illustrates the software main screen which appears on a pc monitor when loaded, featuring an "information bar" of function buttons and a "button bar."

The electronic goniometer (EG) may be used to provide extremity range of motion measurements in exact accordance with the American Medical Association's (AMA) standards that are found in its publication, Guides to the Evaluation of Permanent Impairment. The digital EG does not need to be calibrated, but may be checked using the EG tab 53 on the utility window 50 (FIG. 13). When seeking to calibrate the analog set of goniometers, and after selecting the EG tab 53, the utility screen 50 will again display a re-calibrate button 65 (FIG. 14). As with the hand dynamometer, the re-calibrate button 65 will then be replaced by a message area that also has an "OK" button and a "cancel" button. The message area for the analog EG will then say "set Goniometer to CLOSED Position (0 Degrees)." The goniometer should be set to 0° by closing the arms all the way together, and then the "OK" button may be clicked on the screen, or alternatively, a button on the goniometer may be depressed (FIG. 15). Next, the screen will ask for the goniometer to be set to 180°. Set the goniometer to 180° by opening the arms and flattening them out on a flat surface, then click the "OK" button or the button on the goniometer (FIG. 16). The instructions will also then require calibration at 225 degrees and 90 degrees to complete the calibration process (FIGS. 17 and 18). Calibration of the older EG 1040 is the same as for the analog set, except that calibration is done for arm positions of 0 degrees, 90 degrees, and 180 degrees (FIGS. 19-22). An extended heart rate system may also be used with the current invention, and it may be tested for its proper function with the system, by selecting the HR tab 56 on the Utility Screen, as seen in FIG. 23.

Any of the heretofore mentioned pieces of equipment, in addition to other pieces discussed hereinafter, may be utilized for a functional evaluation of a patient. They may be used for new patients, for any of the reasons stated in the earlier paragraphs of the detailed description, but particularly so on a second visit for all new patients exhibiting musculoskeletal injuries, once the doctor has determined a diagnosis. The evaluation may be performed during the middle of treatment to further evaluate the patient's condition, as well as establish further treatment protocols. For surgery patients, the evaluations may establish functional pre-surgery baseline data, for comparison to a patient's post-surgery status and progress in the recovery process.

Figure 73:
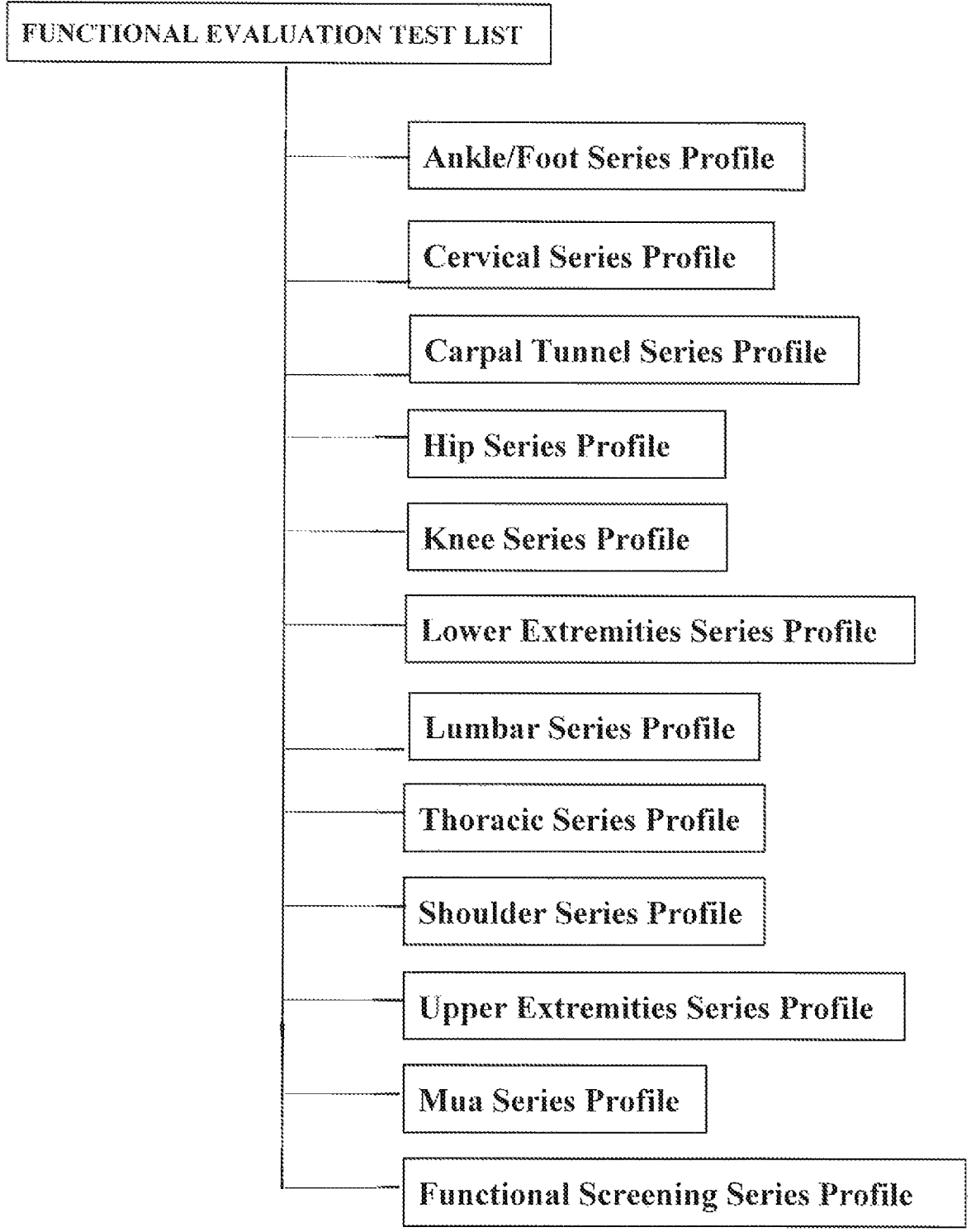
FIG. 73 is a flow chart illustrating the thirteen functional evaluation test series that are available under the software of the current invention.
Figure 75:
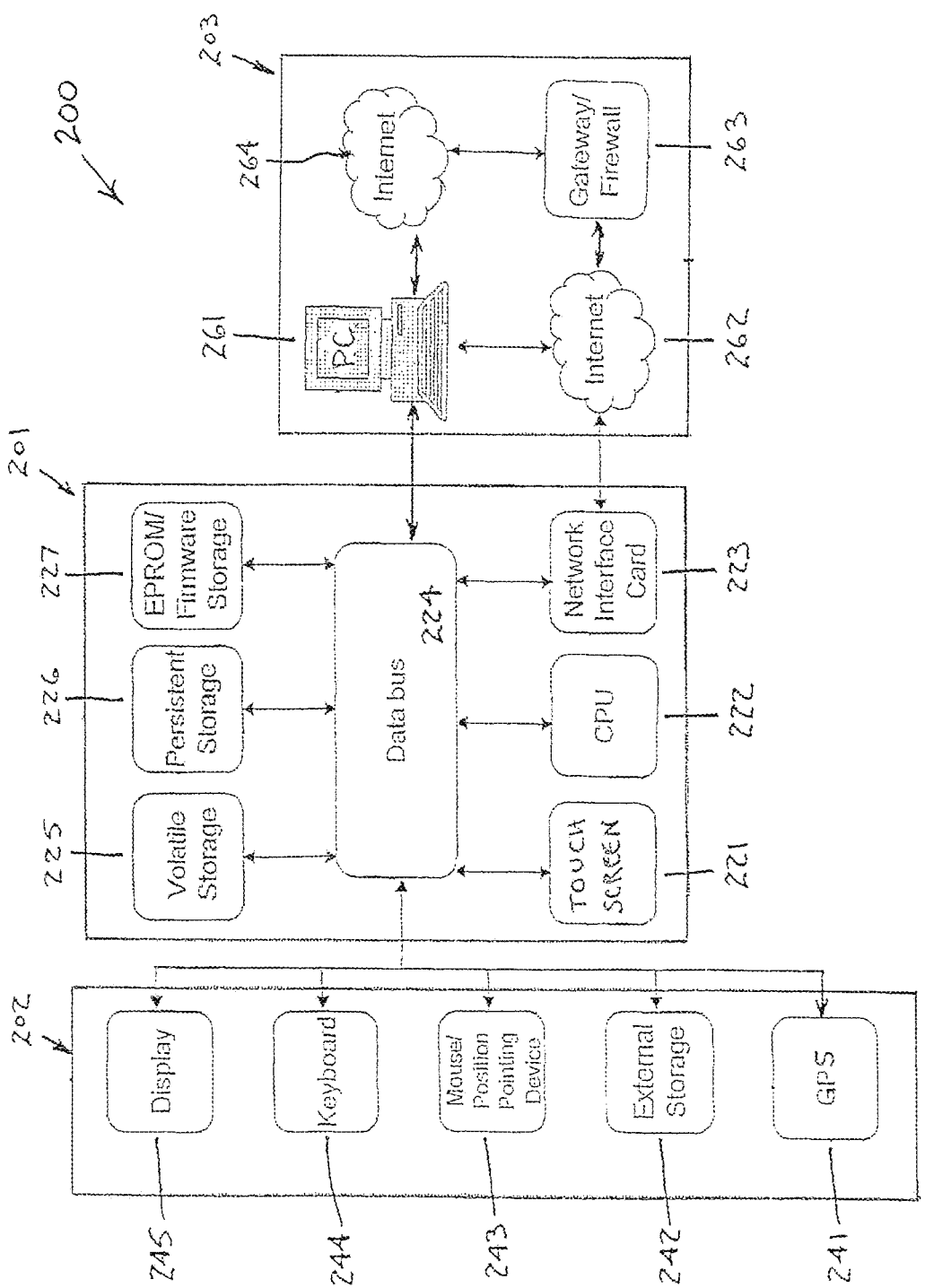
FIG. 75 is a schematic of an exemplary computer system.

There are many protocols of tests available in the current invention, including, but not limited to: an Ankle/Foot Series Profile; a Cervical Series Profile; a Cervical/Wrist Series Profile; an Elbow Series Profile; a Hip Series Profile; a Knee Series Profile; a Lumbar Series Profile; a Lower Extremity Series Profile; a Shoulder Series Profile; a Thoracic Series Profile; an Upper Extremity Profile; and a Wrist/Carpal Tunnel Series Profile. The reasons for ordering each of these protocols may be found in FIG. 73A, Table 1. The profile of tests to be performed for each of those protocols is found in FIGS. 73B to 74K, Tables 2-14. The prefix before each test in those charts corresponds to the test/equipment used, with EG being electronic goniometer, RM being range or motion, PG being pinch gauge, etc. The tests are generally known to persons skilled in the relevant art, and therefore the sequence of instructions for each, and/or a discussion of each, is not required to disclose the invention herein. However, to be illustrative, FIG. 74 depicts the first six tests performed in the Cervical Series Profile of FIG. 73C, Table 3.

To ensure the validity of the method herein, the tests may be conducted in accordance with the requirements of the AMA Guides' $2^{nd}$, $3^{rd}$, $4^{th}$, $5^{th}$, or $6^{th}$ editions, the disclosures of which are incorporated herein by reference. Generally, the AMA's guides specify that spinal range of motion (ROM) measurements are to be repeated until three consecutive measurements fall within a specified range of one another. If this does not occur within a total of six measurements, the test is stopped and considered invalid. For the $4^{th}$ Edition "Guides", the specified range is within 5° or 10% (whichever is greater) of the mean (average) measurement. During a range of motion (ROM) testing, validity is achieved when three consecutive trials are found to be within 5° or 10% as described above. If not achieved in trials 1, 2 and 3, then a fourth trial is performed. If not achieved in trials 2, 3 and 4, a fifth, and then a sixth trial is performed, as necessary. If validity is not achieved by the end of the sixth trial, the test is invalid.

Figure 28:
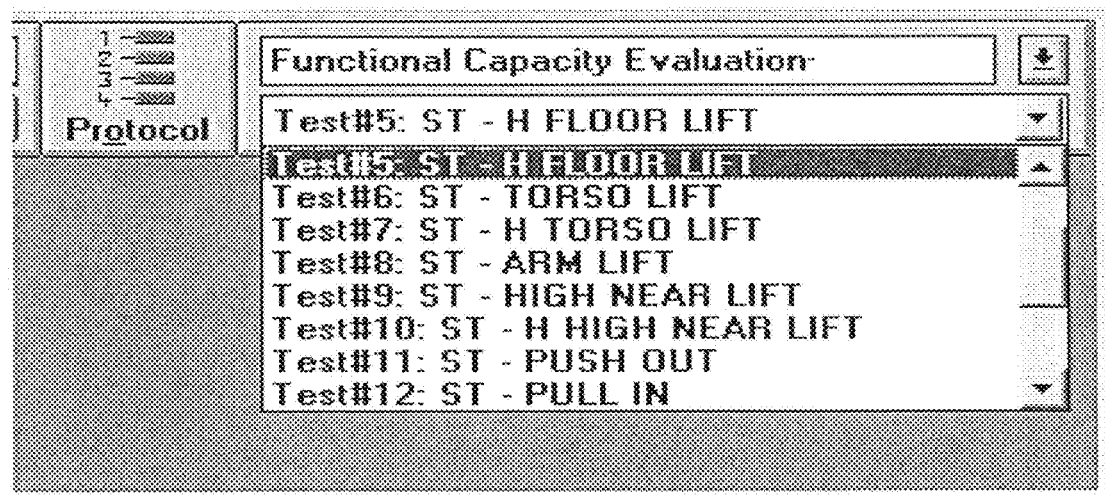
FIG. 28 illustrates choosing to run a test while inside a protocol by dropping down the test menu.
Figure 28A:
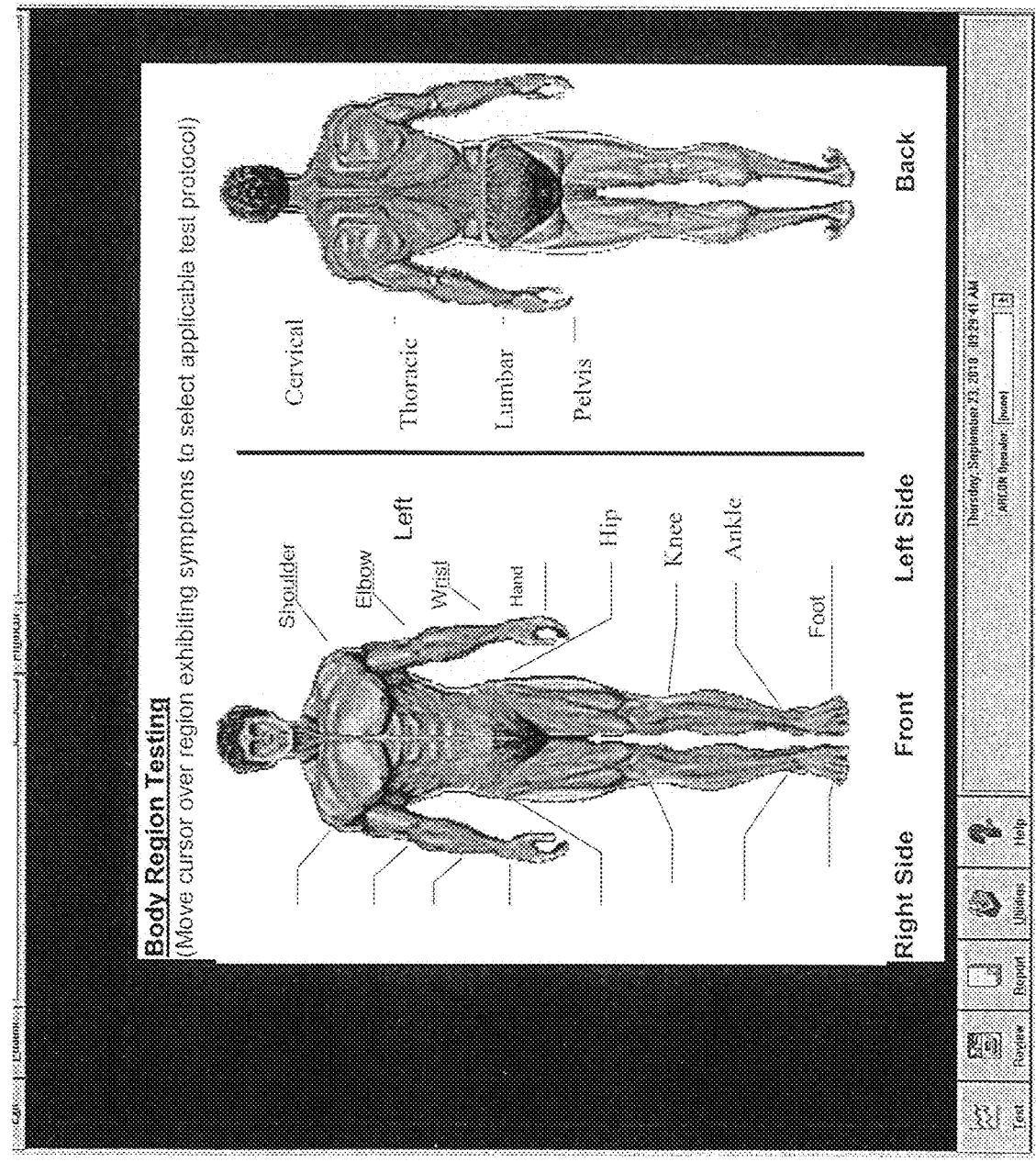
FIG. 28A illustrates choosing to run a test by selecting from, an on-screen pictorial image, a region of a person to be tested from a computer generated image of a man.
Figure 28B:
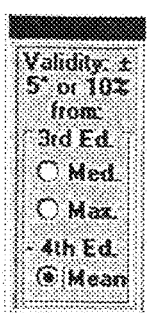
FIG. 28B illustrates a validity option window that may appear when a range of motion test has been selected from the pictorial of FIG. 28A.

An example of the selectable options which may appear upon selection of a ROM test is shown in FIG. 28B, and comprises a window that allows the user to select the manner in which the software determines validity. It permits selection of the standard as being the $3^{rd}$ Edition Median standard, the $3^{rd}$ Edition Maximum standard, and the $4^{th}$ Edition Mean standard. The first option, $3^{rd}$ Ed. Med., uses the median (middle) of the three measurements as the comparison value. If the other two trials are within 5° or 10% of this value then validity is achieved. The second option, $3^{rd}$ Ed. Max., uses the maximum (largest) of the three measurements as the comparison value. If the other two trials are within 5° or 10% of this value then validity is achieved. This option is more restrictive than the previous option, so a patient will have to perform more consistently to achieve validity. The bottom option shown, $4^{th}$ Ed. Mean, uses the mean (average) of the three measurements as the comparison value. If the other two trials are within 5° or 10% of this value then validity is achieved. This option is similar to the median option in the $3^{rd}$ Edition "Guides", and is the only option allowed in the $4^{th}$ Edition.

Once a Range of Motion test has been performed, the validity option may not be changed; therefore the option should be set correctly before starting the test. It is also worth noting that this option will remain set to whichever method is selected for subsequent ROM tests. Also, one additional validity check is performed for Lumbar Flexion/Extension tests—the total sacral flexion/extension (the movement measured by a ROM sensor #2) is compared with the tightest (smallest) straight leg raise. If the straight leg raise is more than 10 degrees (15 degrees in the $4^{th}$ Edition)

larger than the total sacral flexion/extension, the Lumbar Flexion and Extension measurements are considered invalid.

Figure 30:
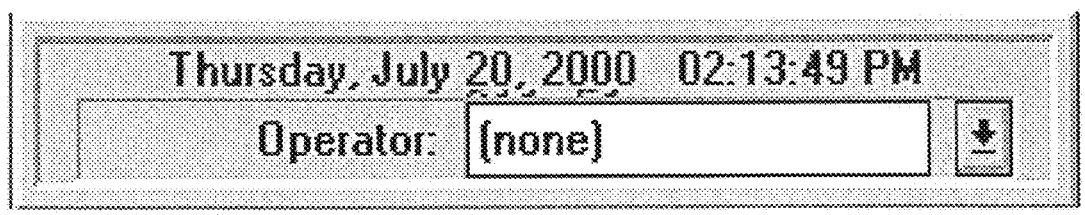
FIG. 30 highlights the "operator" drop down option on the button bar of FIG. 24.
Figure 34:
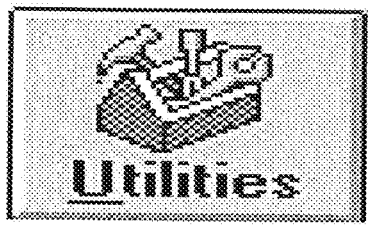
FIG. 34 highlights the "utilities" button of the button bar of FIG. 24.
Figure 35:
FIG. 35 highlights the "help" button of the button bar of FIG. 24.

Once it has been determined that a patient requires testing, and the software of the current invention has been opened on computer system 11, the user may toggle the operator drop-down panel 37 (FIGS. 2 and 30). The Operator "drop-down" is used to select the current Healthcare operator. If the system is to be left unattended, the operator should be set to "(none)" to prevent tests from being accidentally run using the wrong operator's name. The information for each operator must first be entered using the Utility button (FIG. 34). The Utilities Button is used to perform a number of "housekeeping" functions associated with the system software. The most important is calibration of the Healthcare testing instruments, but other functions include backup (making a copy of your database for safe keeping), entering information on Professional Healthcare operators, setting certain system options, and running a test program to check system components.

Figure 25:
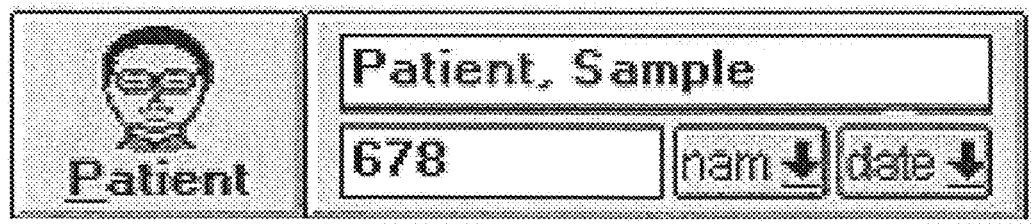
FIG. 25 illustrates the patient panel portion of the information bar of FIG. 24.
Figure 36:
FIG. 36 highlights the "patent" database button of the patient panel of FIGS. 25 and 26.
Figure 37:
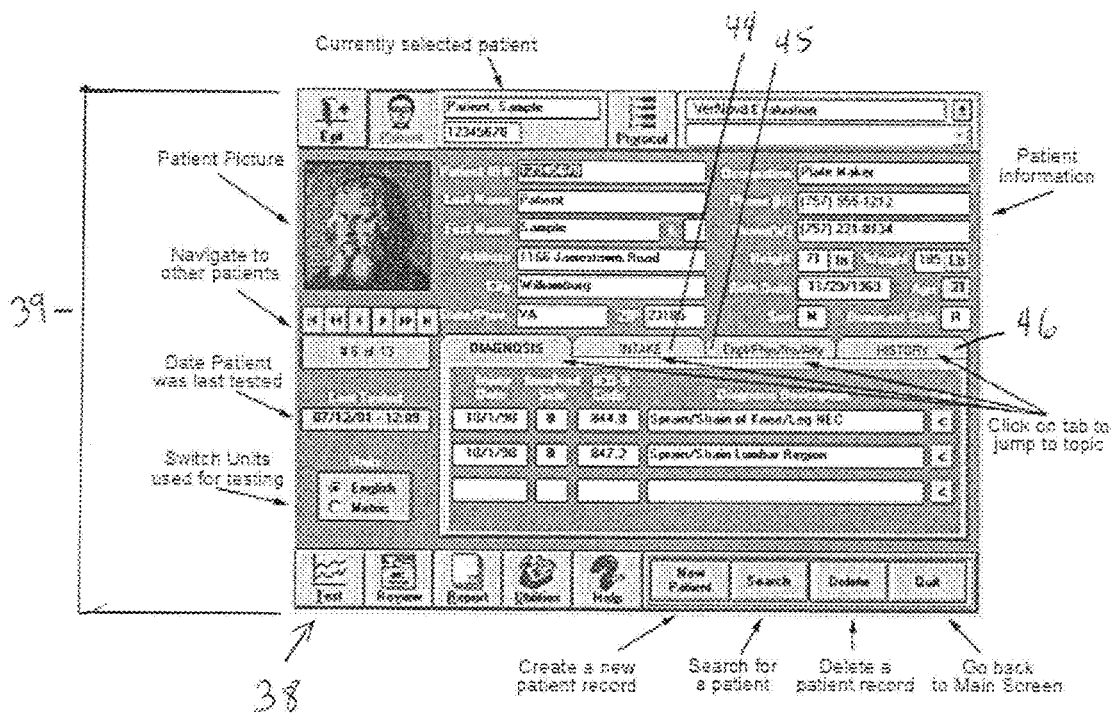
FIG. 37 illustrates the patient database window accessible using the patient data base button of FIG. 36.

Next, the patient button 26 (FIG. 36) of the patient panel 25 (FIGS. 2 and 25) may be clicked on, to access the patient database screen 38 of FIG. 37. It may also be accessed by pressing "P" on the keyboard. The patient database screen is used when accessing or updating the Patient Database. It allows the user to add a patient to the database, to delete a patient, to examine and/or change information for existing patients, or to search for a patient using a specific item of information. All the information for a single patient is stored in one record in the database.

The patient database screen, as seen in FIG. 37, comprises the information bar and button bar separated by a patient record panel 39. Clicking on the patient button 26 may also cause replacement of the operator drop-down panel 37 in the button bar 22 with a series of patient-specific buttons, which are highlighted in FIG. 38 and are used to control the Patient Database Screen. The buttons, which may include new patient button 40, search button 41, delete button 42, and quit button 43, give the user the ability to add a New record, Search for an existing record (or set of records with selected items in common). Delete a record or Quit the Patient Database Screen and return to the Main Professional Healthcare Screen. Clicking on the search button 41 may permit the operator to retrieve a patient record, by I.D. number or name, etc., as seen in FIG. 37. Clicking on the new patient button 40 (FIGS. 37-39) creates a new (empty) patient record in the database, and then waits for the operator to enter the information for the new patient. The active portion of the screen will change to appear as shown in FIG. 40. In the patient record screen, each white box is a separate item or field. The cursor is positioned at the first field, Patient ID #, waiting for that information to be entered. The user may type an ID number for the patient (e.g. the patient's SSN) and then press the Enter key to enter this item, and move on to fill in the other fields.

Figure 41:
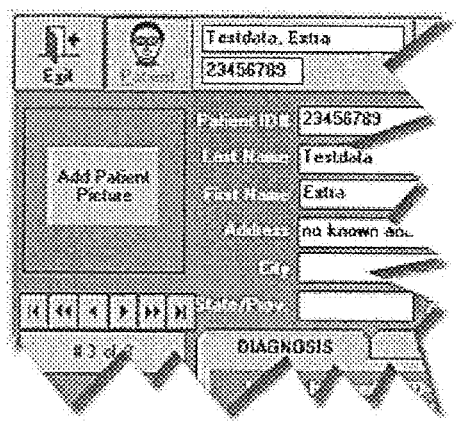
FIG. 41 highlights the patient picture portion of the patient database window of FIG. 37.
Figure 42:
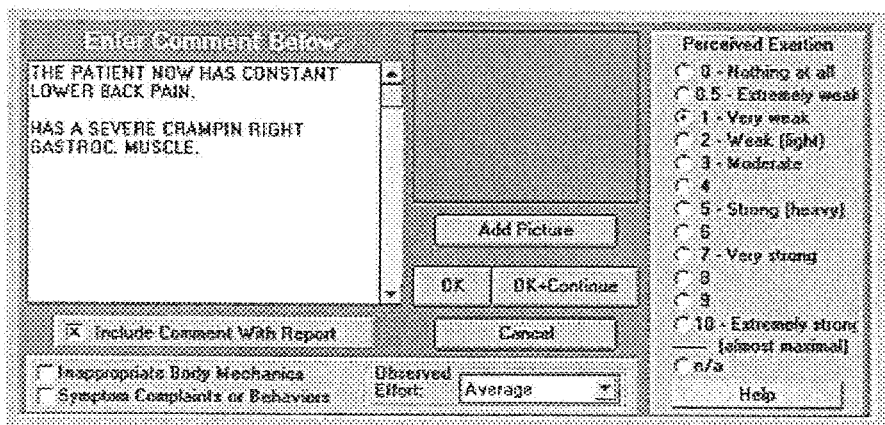
FIG. 42 highlights patient picture option available after a test of FIG. 28.
Figure 43:
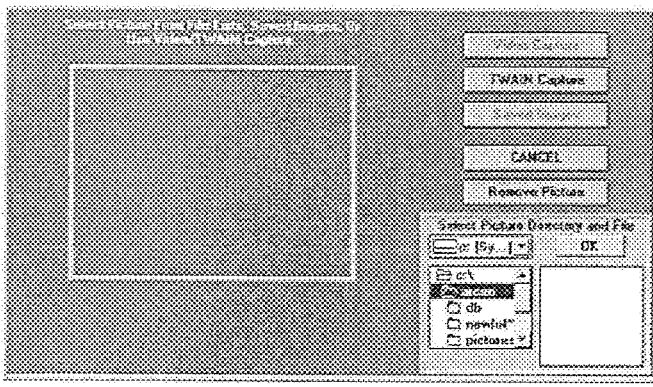
FIG. 43 highlights the option for replacing a patient picture.
Figure 44:
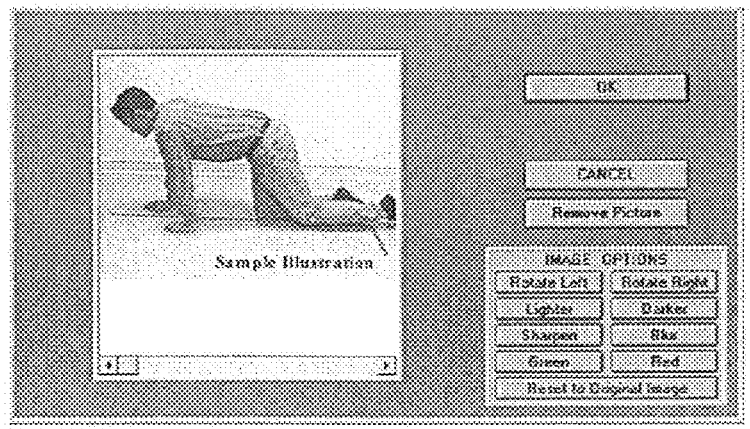
FIG. 44 highlights the option for modifying a patient picture.

The software has the capability of inputting patient pictures into two different parts of the report. The first is in the patient information section (FIG. 41), and the second is inside each comment that is available after each test, and where the picture may be added by clicking the "Add Picture" button (FIG. 42). To change or modify a picture, double click the current picture, which causes the window pictured in FIG. 43 to appear, providing selectable options for the source of the image file. There are two methods of importing images into the system—either from a file or floppy disk. The recommended digital camera for use with the system is a Sony Mavica, which uses a floppy disk to store images. To load an image from a floppy, the user may place the floppy disk into the computer and select the "a" drive from the drop down in the bottom right corner, and then click on the image to select it. The software also provides options for modifying a patient picture. After selecting a patient image, a new screen will appear (FIG. 44) allowing the user to center, to rotate, and to color correct the image. If the editing results are unsatisfactory, the user may click the "Reset to Original Image" button. To completely remove the image from the record, the user may click "Remove Picture." When an image is satisfactorily edited, click the OK button, which returns the operator back to the patient screen, where the image will be displayed.

Figure 45:
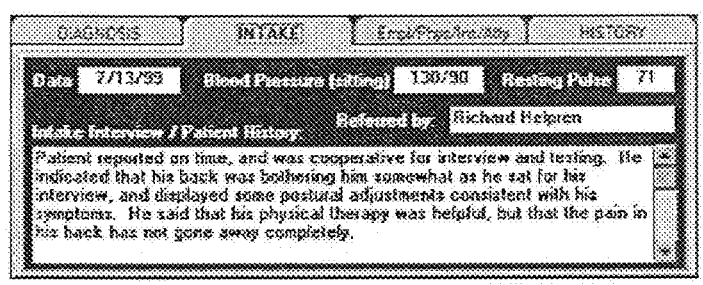
FIG. 45 highlights the intake screen portion of the patient database window of FIG. 37.

Next, an "Intake" tab 44 on FIG. 37 may be toggled to reveal the Intake screen of FIG. 45, which may contain standard information that is normally collected when seeing a new patient, such as: Blood Pressure, Resting Pulse and Referred by are optional. The Intake Interview/Patient History is a large field designed to contain patient information that is to be included in the final report. The field can contain up to 65,000 characters or several pages of text.

Figure 46:
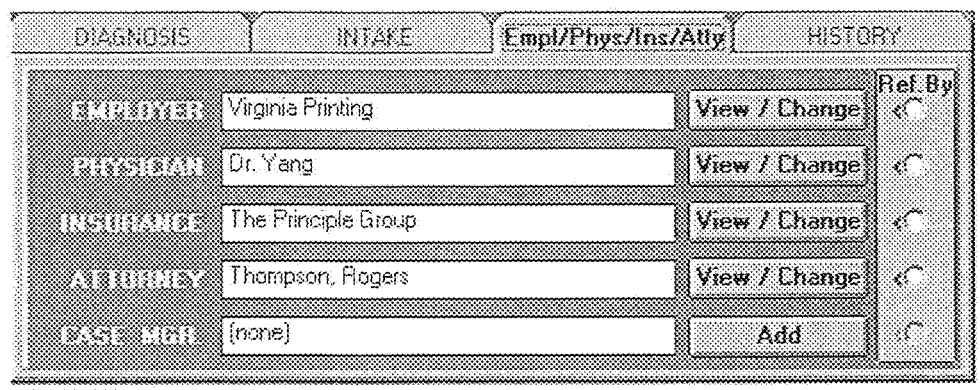
FIG. 46 illustrates the "Empl/Phys/Ilns/Atty" tab of The Patient Database Screen of FIG. 76.
Figure 47:
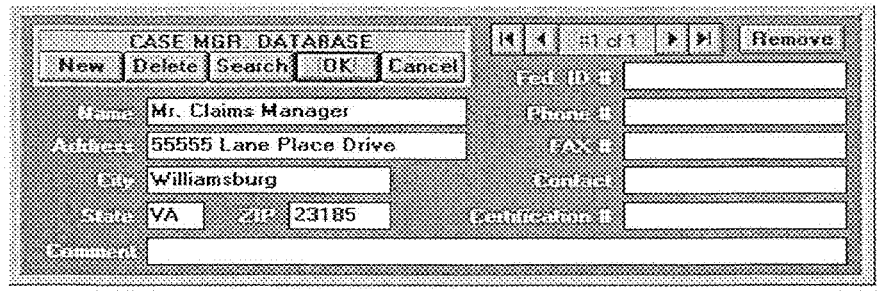
FIG. 47 illustrates the contact window option when add under the "Empl/Phys/Ins/Atty" Tab of FIG. 46.
Figure 48:
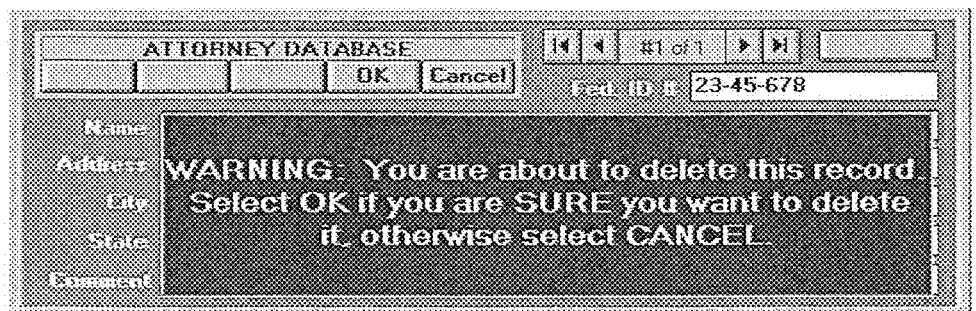
FIG. 48 illustrates the warning screen that is displayed when attempting to delete a contact from a patient database.

Also, the "Empl/Phys/ns/Atty" tab 45 of FIG. 37 may be toggled to reveal the corresponding screen, as seen in FIG. 46. The screen may be used to enter Employer, Physician, Insurance, Attorney, and Case Manager Information. Contacts that are already selected from within the database have a "View/Change" button next to them. To change, remove, or create a new contact, the user may click the "View/Change" button and follow the previous steps. If a contact has not yet been selected, the user may click the Add button, which will open the window of FIG. 47, allowing the user to select a current contact within the database, or create a new contact. The user may click the "Ref." button to denote that this contact has referred the patient. To select a current contact, the user may navigate to it with the VCR type interface on the top right portion and select the "OK" button in the top left. A new contact may be created by clicking the "New" button, by typing in the contact information, and then clicking the OK button to select it. To remove the link between the contact and the patient record, the user may click the Remove button in the upper right hand corner. To delete a contact from the entire Professional Healthcare database, the user may click the Delete button in the upper left corner. Doing so will cause a warning screen, as seen in FIG. 48, to appear, since deleting a contact from the database will remove it from every patient record that uses it.

Figure 49:
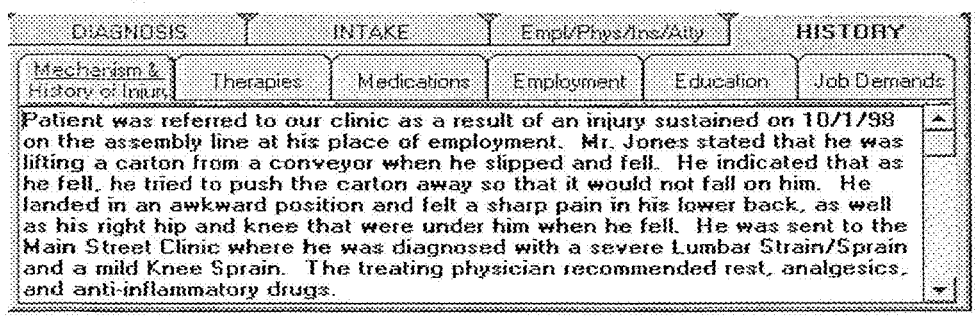
FIG. 49 illustrates the "history" tab of The Patient Database Screen of FIG. 76.

Hitting the History tab 46 in FIG. 37 may cause the History screen of FIG. 49 to appear. The history tab contains sub-tabs that allow you to record the tab-specific information for the patient, such as "Mechanism and History of Injury," "Therapies," "Medications," "Employment," "Education," and "Job Demands."

Figure 50:
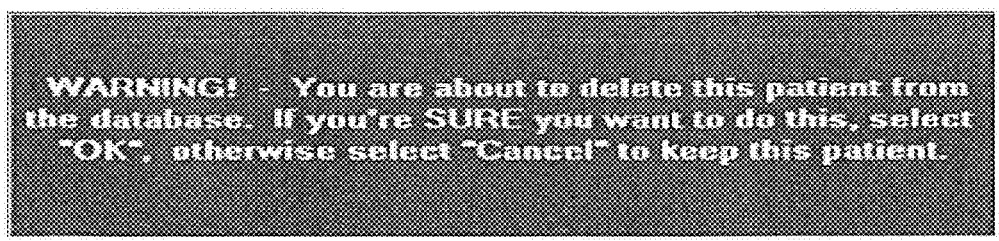
FIG. 50 illustrates the warning screen displayed when attempting to delete records from the patient database.

Patient records may be deleted from the Patient Database, by finding the record to be deleted either by using the Search function or by using the VCR control. The user should make sure that the record to be deleted is the "active" record—the one that is being displayed in the Patient Database screen, and then click the Delete Button on the lower right side of the Button Bar. A warning box, shown in FIG. 50, will be displayed. If the displayed record is definitely the one to be deleted, then the user may click the OK Button in the option panel, otherwise the Cancel button should instead be clicked.

Figure 26:
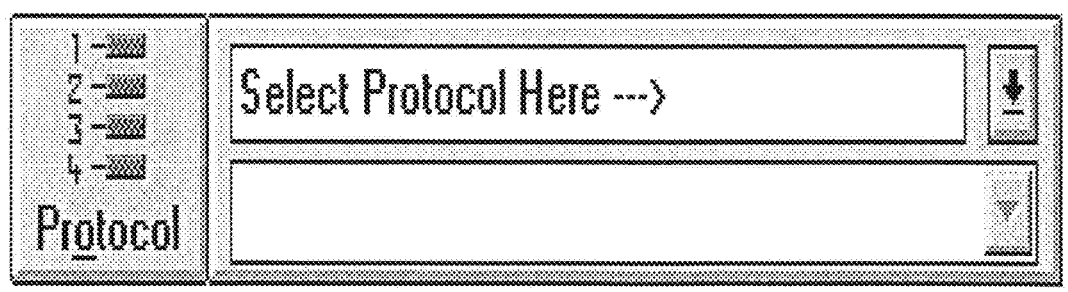
FIG. 26 illustrates the protocol panel of the information bar of FIG. 24.
Figure 27:
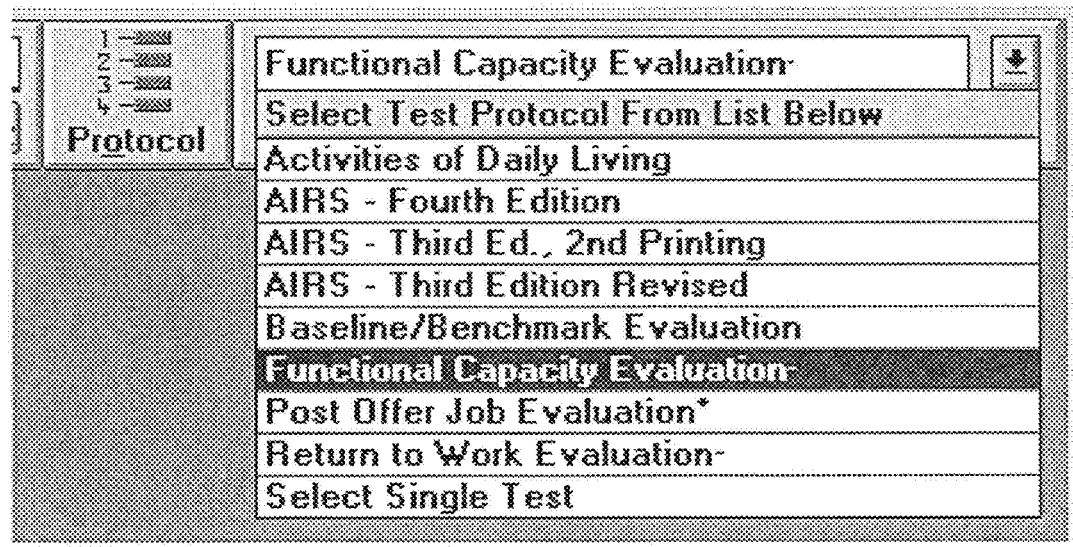
FIG. 27 illustrates the drop-down protocol list available under the protocol panel of FIG. 65.

Once a patient record has been established, testing may begin on a patient. For an existing patient, the operator need only select the patient. First, a testing protocol must be selected. The term protocol may refer to a step-by-step set of "instructions" for testing a patient. A protocol can be as simple as a single test (a hand dynamometer test), or it may contain a number of tests (a total spine range of motion evaluation). Protocols thus provide a method for grouping and sequencing the steps involved in a patient evaluation. The software system includes a comprehensive set of pre-defined protocols. Users may also create new protocols, or modify existing protocols to meet specific requirements, using the large "Protocol" button in the Protocol panel of FIG. 26. A predefined protocol may be selected from the protocol panel 30, using the Protocol Drop-down list, as seen in FIG. 27. (Note—the protocol button 29 in FIG. 2 is for adding a custom protocol to the system.) Also note that, as seen in FIG. 28B, the software provides the option of selectively evaluating the test results according to the various editions of the AMA guides, or other standards.

Figure 28C:
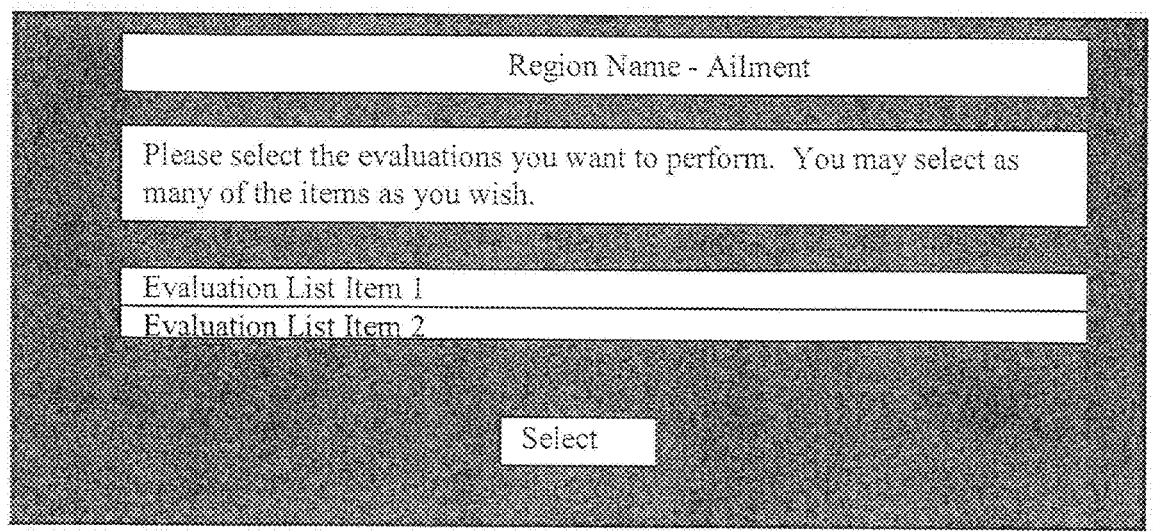
FIG. 28C illustrates an evaluation window with an evaluation test list that may appear when a region has been selected from the pictorial of FIG. 28A.
Figure 28D:
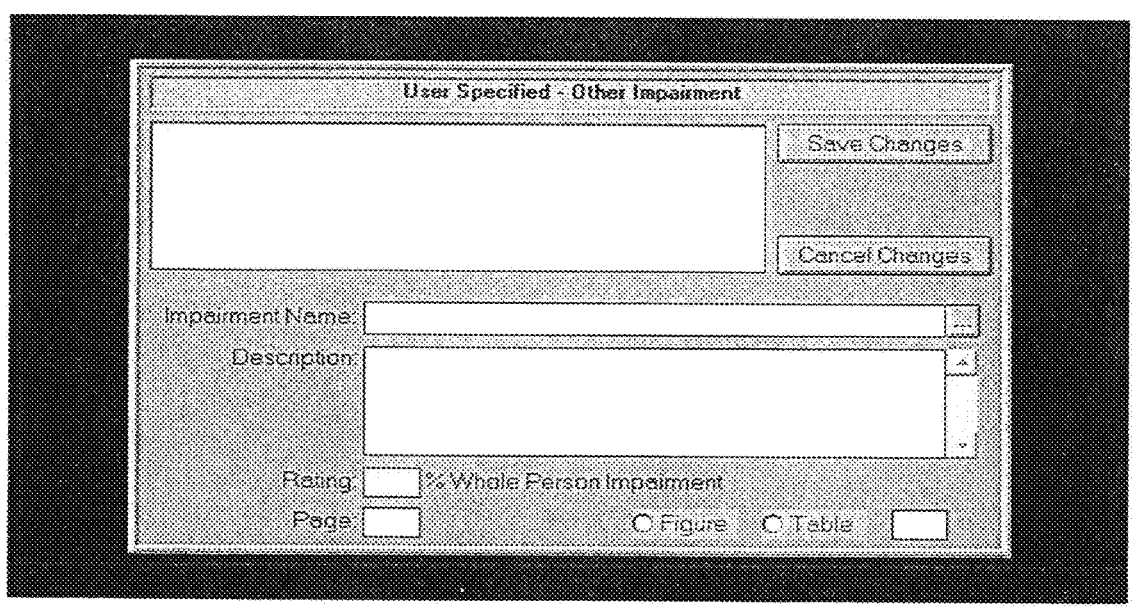
FIG. 28D illustrates a user specified impairment data entry screen.
Figure 28E:
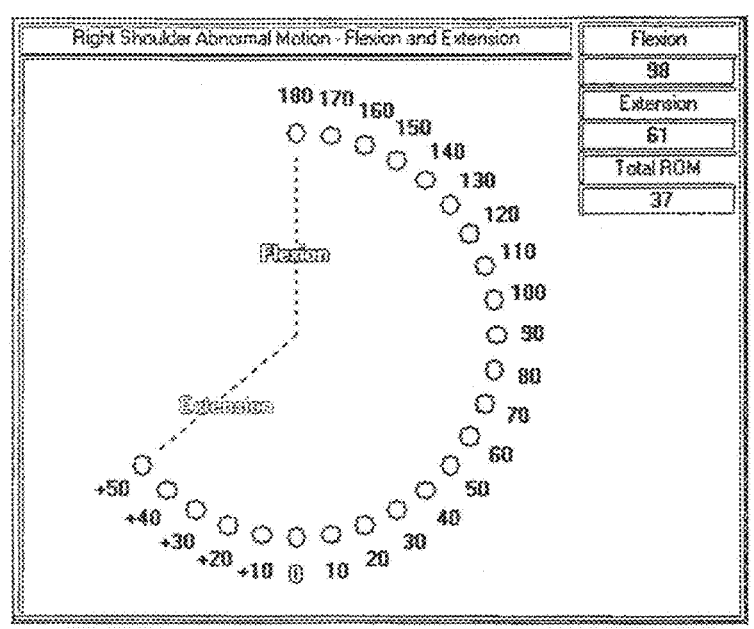
FIG. 28E illustrates a range of motion chart for shoulder flexion and extension.
Figure 28F:
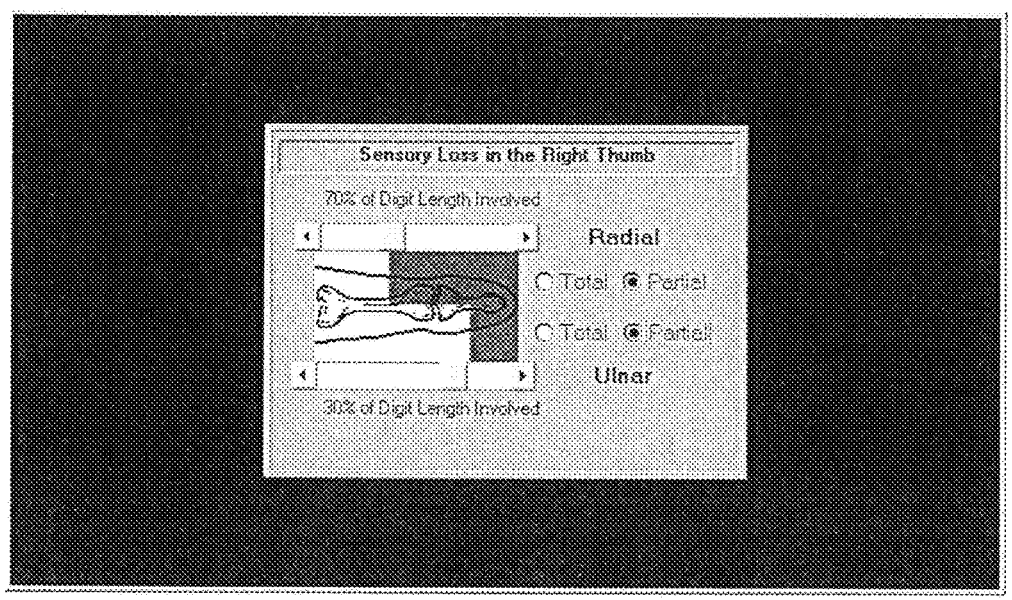
FIG. 28F illustrates a finger evaluation screen.
Figure 28G:
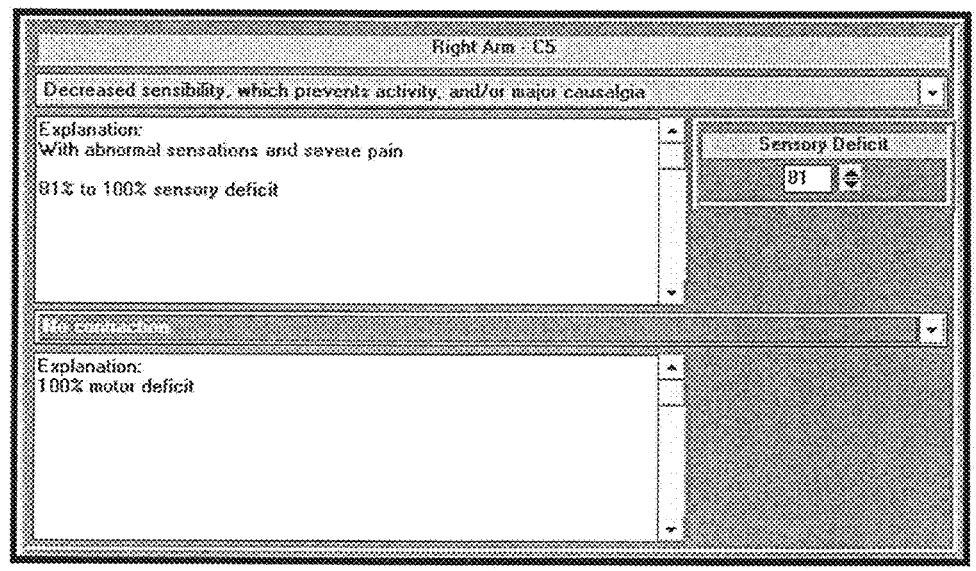
FIG. 28G illustrates an arm evaluation screen.
Figure 28H:
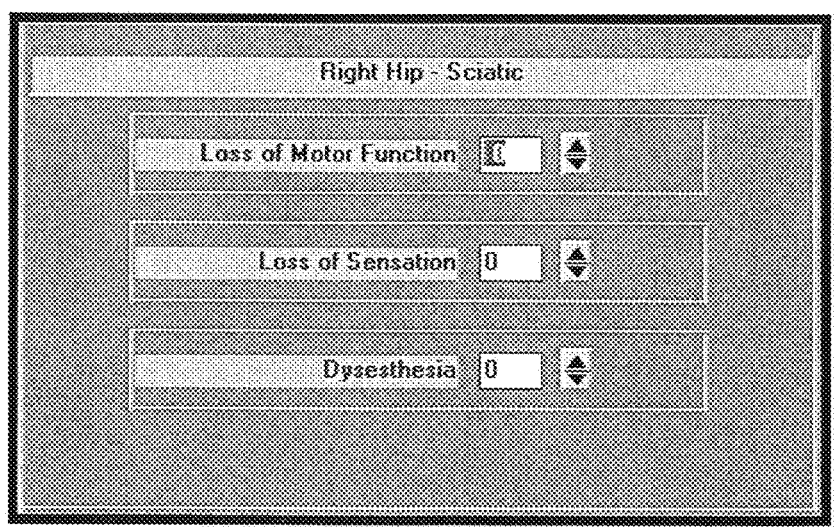
FIG. 28H illustrates a hip evaluation screen.
Figure 28I:
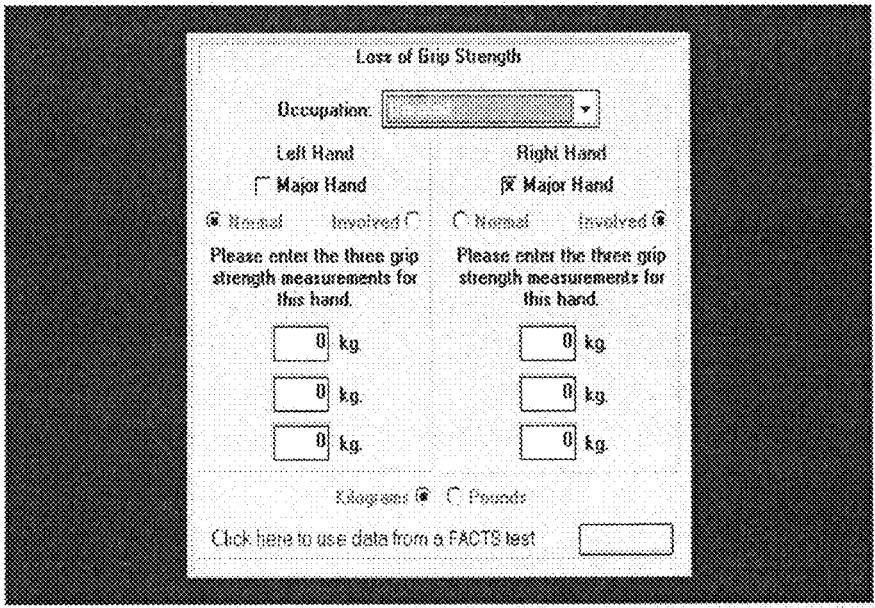
FIG. 28I illustrates a hand grip strength evaluation screen.
Figure 29:
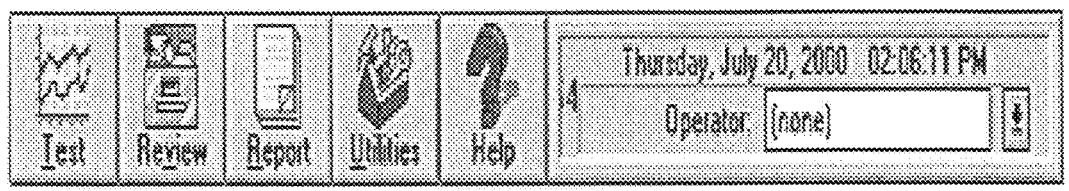
FIG. 29 highlights the buttons and options on the button bar of FIG. 24.

Once the protocol is selected, the user may next select the test from the test window 31 (FIG. 28). Alternatively, a computer generated image of a man may be utilized—for selecting the separate regions of a person which may be subjected to a protocol of tests (FIG. 28A). When using this alternative method, the user can hover over specified regions of the computer generated person and click on a region to display a menu of ailments to evaluate. As the user hovers, the regions are highlighted. A region remains highlighted if ailments have been selected in that region. When a menu option is selected, it appears on the Evaluation List. When a selected menu option is subsequently clicked again, it is removed from the Evaluation List. Each item is displayed in the Evaluation List (FIG. 28C).

The user may click the "Accept" button when all desired regions have been added to the Evaluation List. This will trigger the start of the evaluation process. The process starts by looping through each evaluation test listed in the Evaluation List by selecting individual tests from a series of tests available for that particular region and ailment. The basic format for this process is to display a screen indicating the region and ailment at the top, a middle text region indicating the instructions for selecting the evaluations, and a list of evaluations to be selected at the bottom. A "Select All" button is also provided so the user may easily select all evaluations in the list. The basic format is illustrated in FIG. 28C. As an example, for selection of the Right or Left Shoulders, the evaluation list items may include:

1. Glenohumeral Joint Crepitation
2. Acromioclavicular Joint Crepitation
3. Glenohumeral Synovial Hypertrophy
4. Acromioclavicular Synovial Hypertrophy
5. Glenohumeral Joint Subluxation or Dislocation
6. Acromiclavicular Joint Subluxation or Dislocation
7. Glenohumeral Joint Mediolateral Instability
8. Acromioclavicular Joint Mediolateral Instability
9. Total Shoulder Resection Arthroplasty
10. Total Shoulder Implant Arthroplasty
11. Distal Clavical Resection Arthroplasty When an evaluation is selected for a given Region Name/Ailment and the Accept button is selected, the user has the option to input data for each evaluation. For all data input screens, clicking the main "Accept" button will save the data entered for that evaluation and will navigate to the next evaluation input screen. Also, for each evaluation the buttons "Skip Test" and "Skip All" will be available for the user. Clicking "Skip Test" performs the same action as clicking "Accept" with the difference being the user does not have to enter any data and any results will not be saved for the particular evaluation. Clicking "Skip Test" also displays a message asking, "Are you sure you want to skip this test?" Clicking "Skip All" skips the remaining series of evaluations and displays the results screen. Clicking "Skip All" also displays a message asking, "Are you sure you want to skip the remaining IMPAIRMENT tests?" When all screens have been exhausted, the results will be displayed. FIGS. 28D, 28E, 28F, 28G, and 28H show examples of some possible evaluations and data entry screens.

Figure 31:
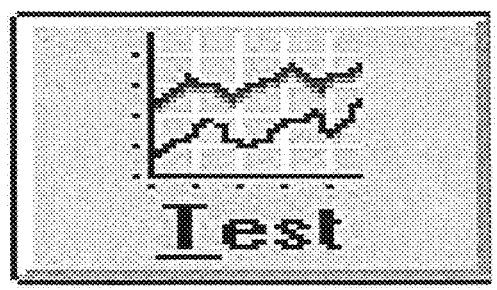
FIG. 31 highlights the "test" button of the button bar of FIG. 24.
Figure 32:
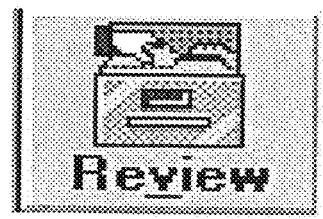
FIG. 32 highlights the "review" button of the button bar of FIG. 24.
Figure 33:
FIG. 33 highlights the "report" button of the button bar of FIG. 24.
Figure 51:
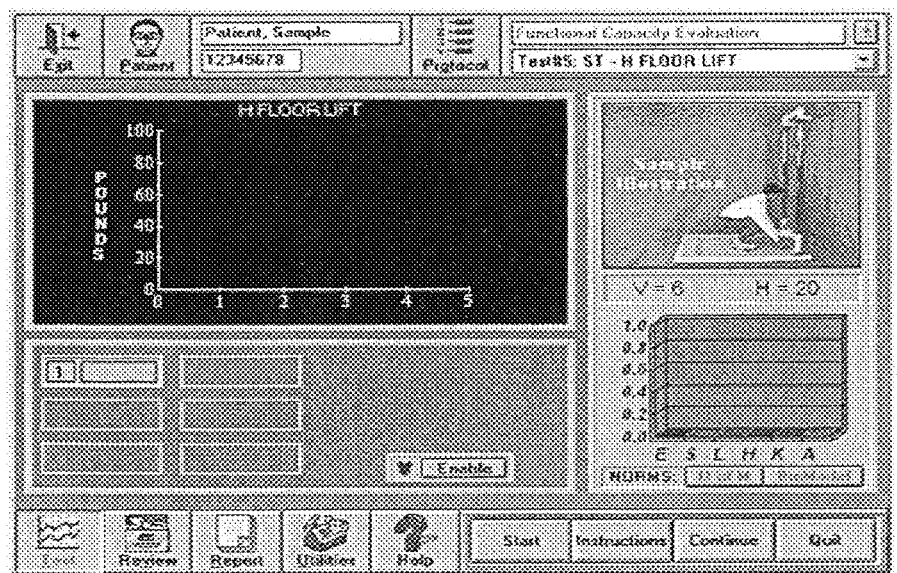
FIG. 51 is illustrative of a test screen for the floor lift test that appears, once a patient and a protocol have been selected and the "Test" button of FIG. 31 has been clicked.
Figure 52:
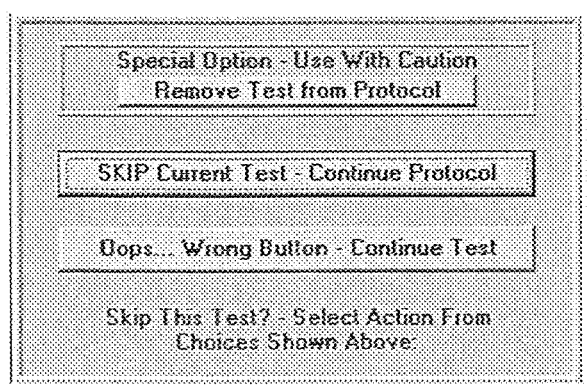
FIG. 52 is illustrates the options available when selecting the "continue" button of the button bar, when in the test screen of FIG. 51.

After the Test Button 32 (FIGS. 2 and 31) is clicked, the Button Bar displays additional buttons in the option panel. An example of a screen from a test is shown in FIG. 51. The test being conducted is the Floor Lift Test, and it is being conducted as part of a Functional Capacity Evaluation Protocol. The added buttons may be on the bottom right and include: "Start," "Instructions," "Continue," and "Quit." They will appear on every type of test screen. Clicking "Start" will start the test and wait for input from the operator or the testing peripheral. Clicking on the "Instructions" button will bring up a screen with instructions for the given test. Every test has instructions and these instructions supply pertinent information such as shelf heights and patient positions. Clicking on the "Continue" button produces the screen of FIG. 52, which will permit the user to click on a "Remove Test" button to remove the particular test from the protocol for this one patient and protocol only. If the user chooses this option, the user will not be able to go back to it later. Clicking the "Skip Current Test" button will move on to the next test in the protocol. This has the advantage of allowing the operator to come back to this test at a later time in order to complete it. If the Continue button was clicked by mistake, then the user may just click the "Oops . . . " button. In FIG. 51, clicking the Quit button will give the user an alert window asking if you are sure, and by clicking "Yes," the user will quit the protocol and be taken back to the main screen. If you quit a protocol, you can continue testing in the same testing record.

Figure 53:
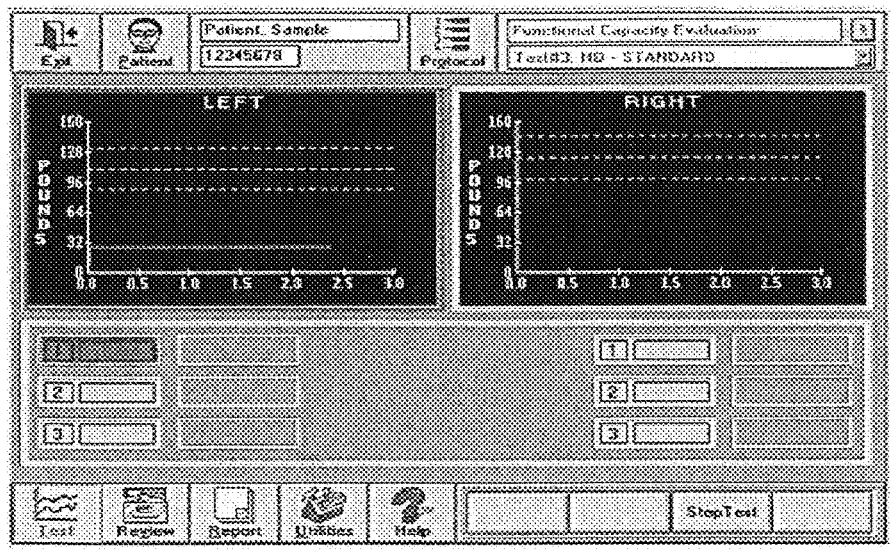
FIG. 53 illustrates the screen displayed when stopping the first trial of a hand dynamometer test.
Figure 54:
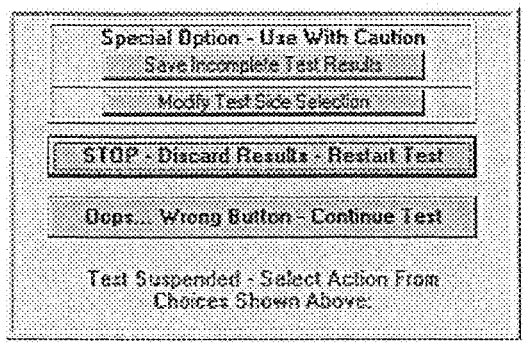
FIG. 54 illustrates the option window displayed after the "stop test" button of FIG. 53 is selected.
Figure 55:
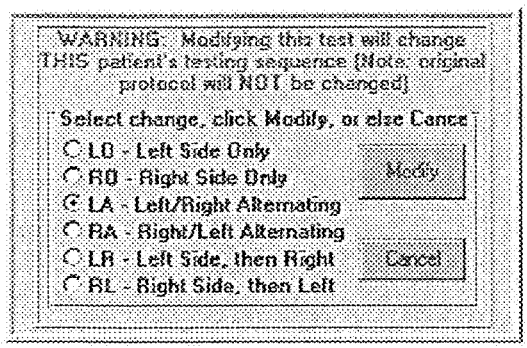
FIG. 55 illustrates the option window displayed after the "Modify Test Side Selection" choice is made on the window of FIG. 54.

FIG. 53 illustrates a standard Hand Dynamometer test in progress as part of a Functional Evaluation. Once the operator has started a test, the trial will highlight and wait for input from the testing peripheral. If the operator needs to stop the test for any reason during the test, the operator may click the Stop Test button on the Button bar. Clicking the Stop Test button will cause the alert window of FIG. 54 to appear. If the "Save Incomplete Test Result" button is clicked, all data from previously completed trails will be saved for the report. This may be necessary if the patient is unsafe, or is unable or unwilling to complete all trails, and the user nonetheless wants the data for the report. The "Modify Test Side Selection" option is only available with the Pinch Strength and Hand Strength protocols, and causes the window in FIG. 55 to appear, and allows the user to modify how the test will run. If the "STOP—Discard Result—Restart Test" button is selected, all data collected from the current test will be dumped and the test will start again, which is useful for instances where there are technical issues or a patient misunderstanding the instructions. The user may click on "Oops . . . Wrong Button," when the operator did not mean to stop the test.

Figure 56:
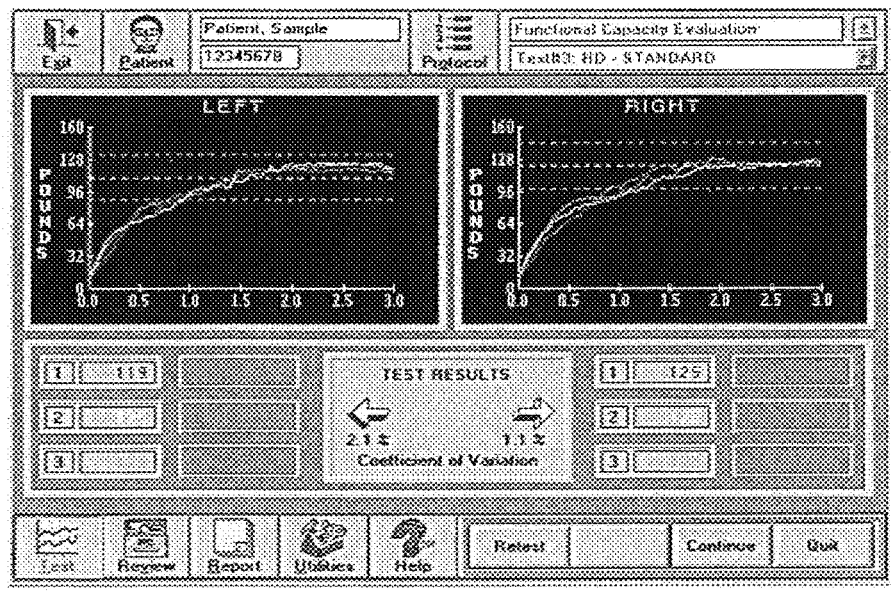
FIG. 56 illustrates the "retest" button displayed during trials of a test being run utilizing the test button of FIG. 31.
Figure 57:
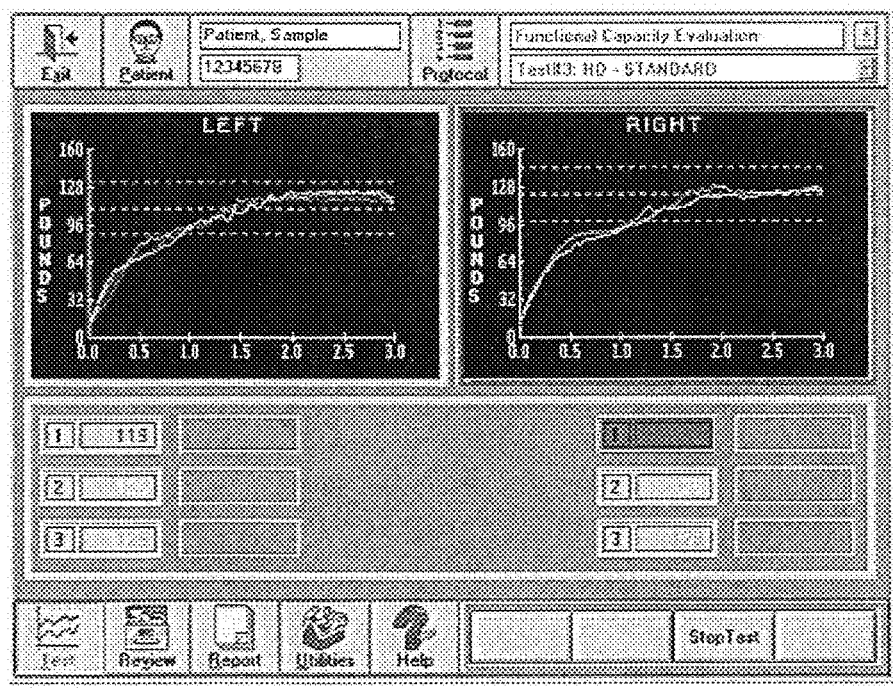
FIG. 57 illustrates selection of a trial to be retested on the screen of FIG. 56.

As seen in FIG. 56, when given trials for a test have been completed, options on the bottom right will appear, including the "Retest" button. In some instances, it may be desirable to retest a trial. Trials should only be retested when a mistake is made or some other non-performance issue has occurred. This feature is not intended to get better results out of a patient. To retest a trial, the operator may click the Retest button on the Button Bar. A message will flash in the middle of the screen asking the operator to select a trial to retest. If the operator selected the number one trial for the right side in FIG. 56, that result window would be become blank, and also be highlighted, as seen in FIG. 57.

Figure 58:
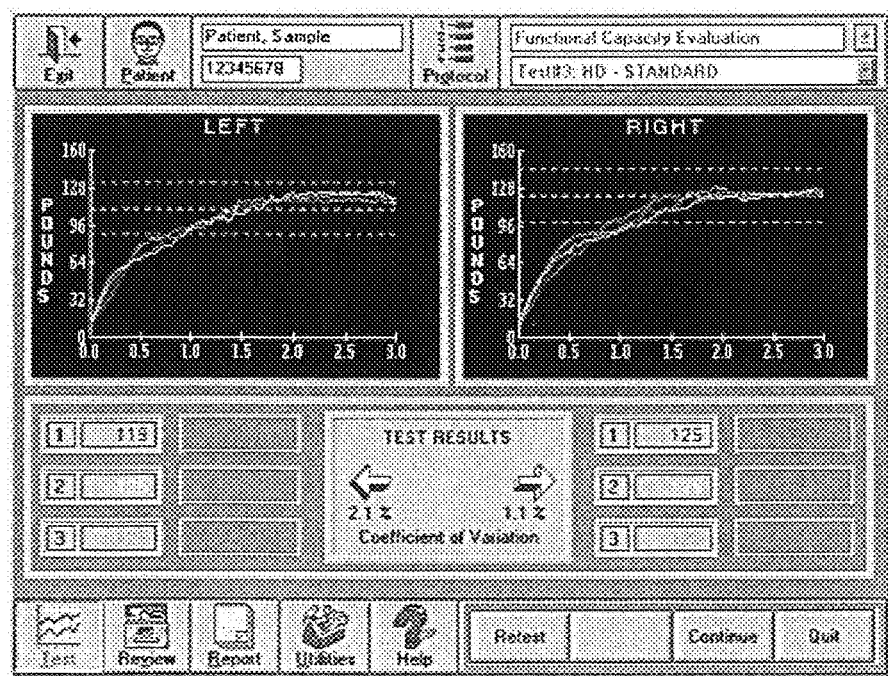
FIG. 58 illustrates appearance of the "continue" button on the button bar after completion of the trials of a test.
Figure 59:
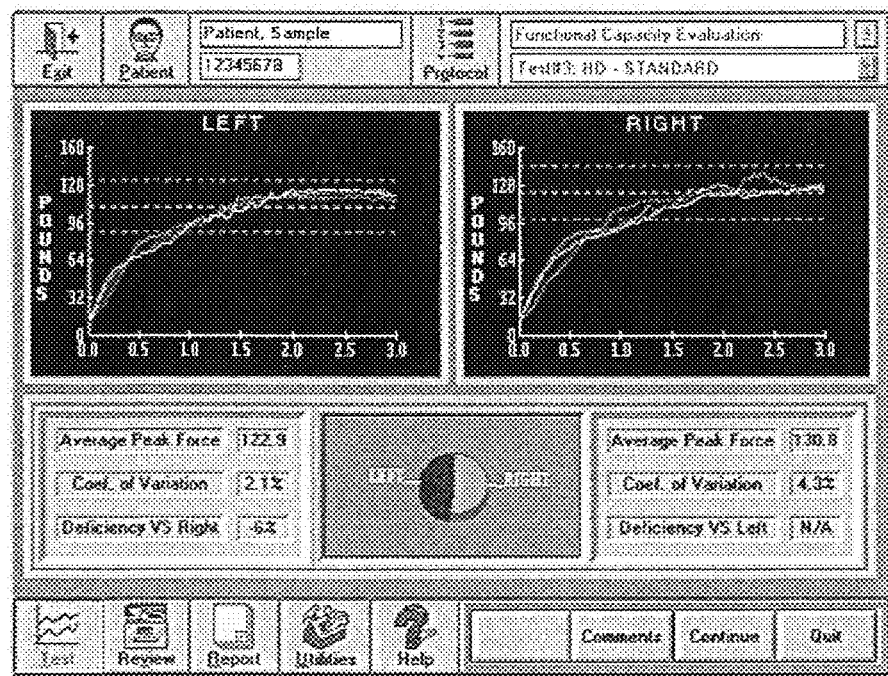
FIG. 59 illustrates the statistical information displayed on the screen as a result of selecting the "continue" button of FIG. 58.

After completion of the retest, the options on the bottom right will again appear, as seen in FIG. 58. It should also be noted that the system will also display a coefficient of variation, in the center of the screen, which will be discussed further in the following paragraphs. The Continue button permits the user to view test statistics, make comments, or continue to the next test in the protocol. If the operator clicked the Continue Button, depending on the type of test, different statistical information may appear on the screen, as seen in the example of FIG. 59. To continue to the next test in the protocol list, the operator may again click the Continue button.

Figure 60:
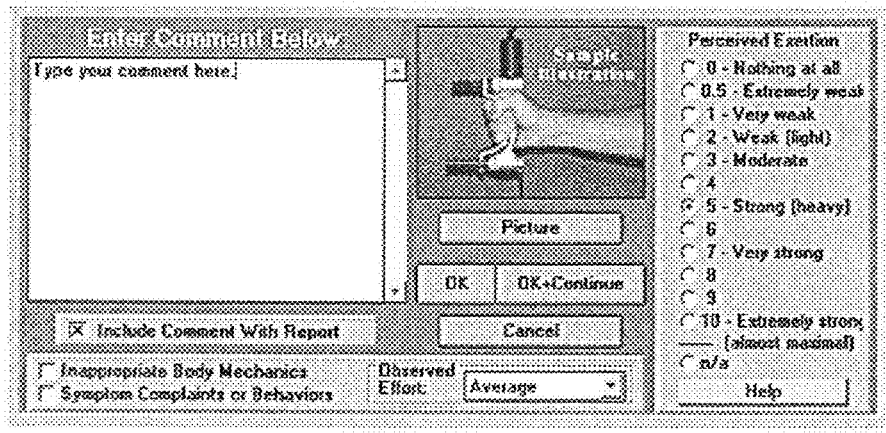
FIG. 60 illustrates the screen displayed when the "comment" button is selected on the screen of FIG. 59.

To make a comment about the current test, the operator may click the Comment button, and type the comment in the white field, as seen in FIG. 60. (Some systems are set up to automatically count down 5 seconds and put up the comment screen.) To see the comment in the final report, select the "Include Comment With Report" option. If the comment is only to be used internally and not be shown in the report, this option should not be checked. On the bottom edge of the comment screen, the user can check that there were Inappropriate Body Mechanics, or Symptom Complaints or Behaviors, or select a level of "Observed Effort," but these options are only used with the MTM Tests. However, on the Right side of the comment screen the user can select a value for the patients "Perceived Exertion." This measure is the patient's response when asked to please rate their own exertion level for this activity. The cumulative responses from this field create a table in the summary section of the report that compares to their heart rate for the given activity. If the user clicks the OK button, the comment will be saved and the user will be taken back to the test results screen. If the user clicks the OK & Continue button, the comment will be saved and the software will move on to the next test in the protocol list. If the Cancel button is clicked, the system will disregard any changes made on the comment screen and return the user back to the test results screen.

Figure 61:
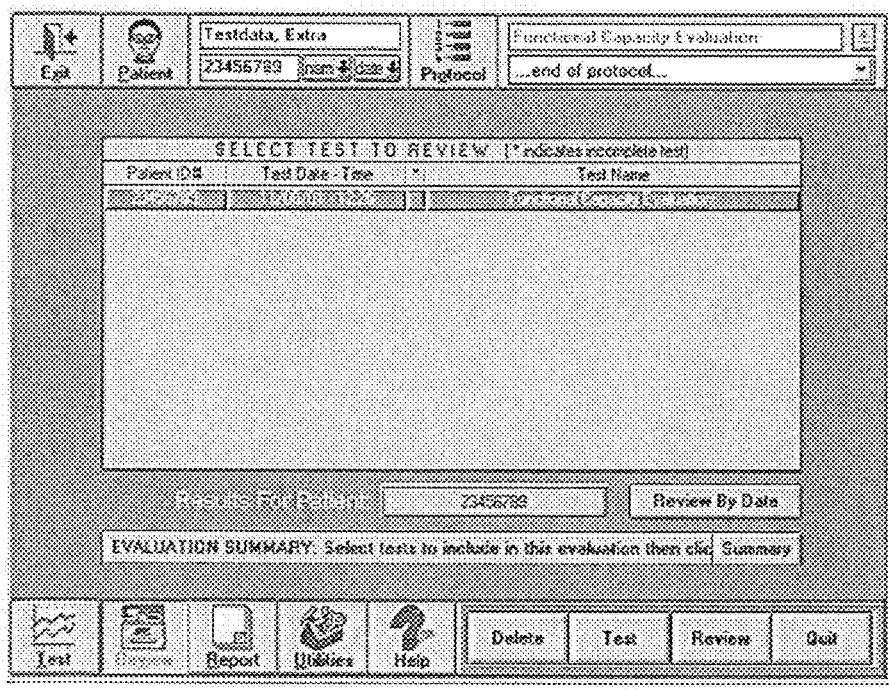
FIG. 61 illustrates the screen displayed after clicking on the "review" button on the button bar.

The Review button is used to review the results of previous tests, or to continue a suspended test—a protocol where one or more steps were skipped or not completed. Test results are displayed for the current patient, but results can optionally be displayed for all patients tested on a given date, which permits an operator to locate test results without remembering a patient's name. To get to the Review Screen, the user may click the Review button with the file icon on the Button Bar in the lower left hand corner on the main screen, as seen in FIG. 61. From the review screen the user can "Create a Summary" for a protocol that was performed; Delete protocols performed from the patient's record; Review results in a protocol & make additional comments; or Quit back to the Main Screen.

Figure 62:
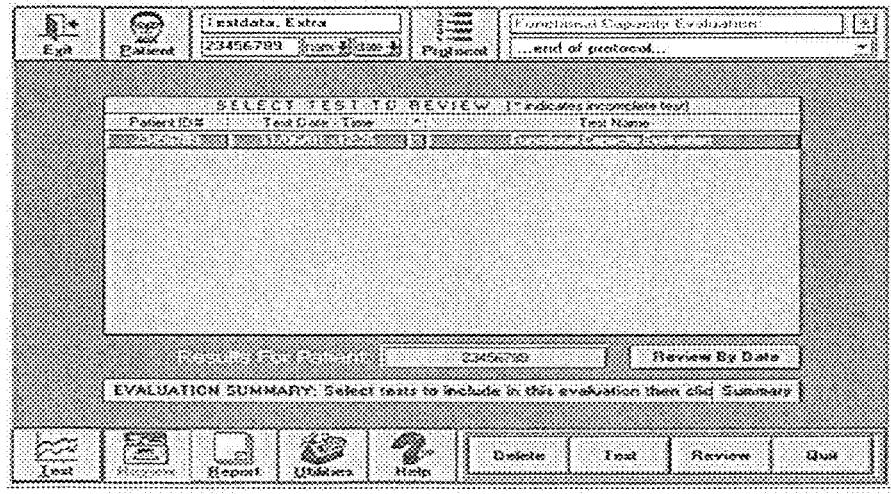
FIG. 62 illustrates selection of an incomplete test for continued testing of a patient while in the "review" screen of FIG. 61.

To return to a protocol to perform a test that was skipped or not completed, the test may be highlighted in the list, as shown in FIG. 62, and then the operator may click the Test button. The software will return to the first incomplete or unfinished test in the protocol list. The test screen will be ready for the patient to start the test. This is currently the only way to continue testing on a protocol that was started and then stopped. The operator should always avoid starting a new protocol in order to have all the data collected appear in one report.

Figure 63:
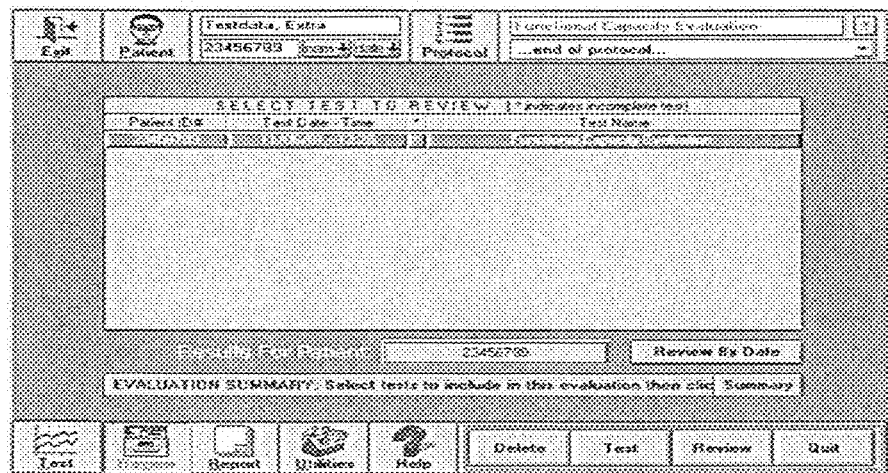
FIG. 63 illustrates the screen selections for deleting a test protocol from a patient's record.
Figure 64:
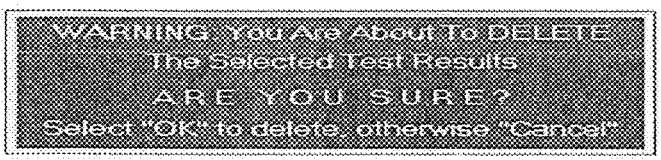
FIG. 64 illustrates a warning screen displayed when deleting the protocol of FIG. 63.
Figure 65:
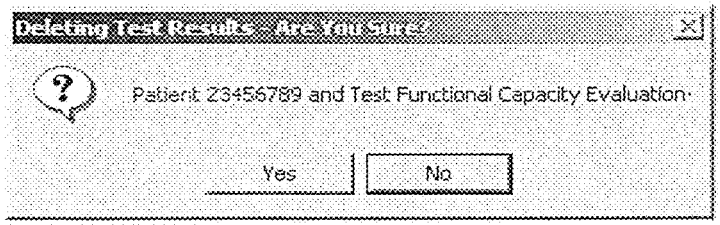
FIG. 65 illustrates the "Yes/No" confirmation screen after receiving the warning in FIG. 103 as to deleting a protocol.

To delete protocols from the patient's records, the protocol may be selected from the list by clicking on it, as seen in FIG. 63, and by next clicking the Delete button. The warning screen shown in FIG. 64 will appear. After reading the warning screen, the user may click OK, and the window shown in FIG. 65 will open to make sure that the operator wants to delete the record.

Figure 66:
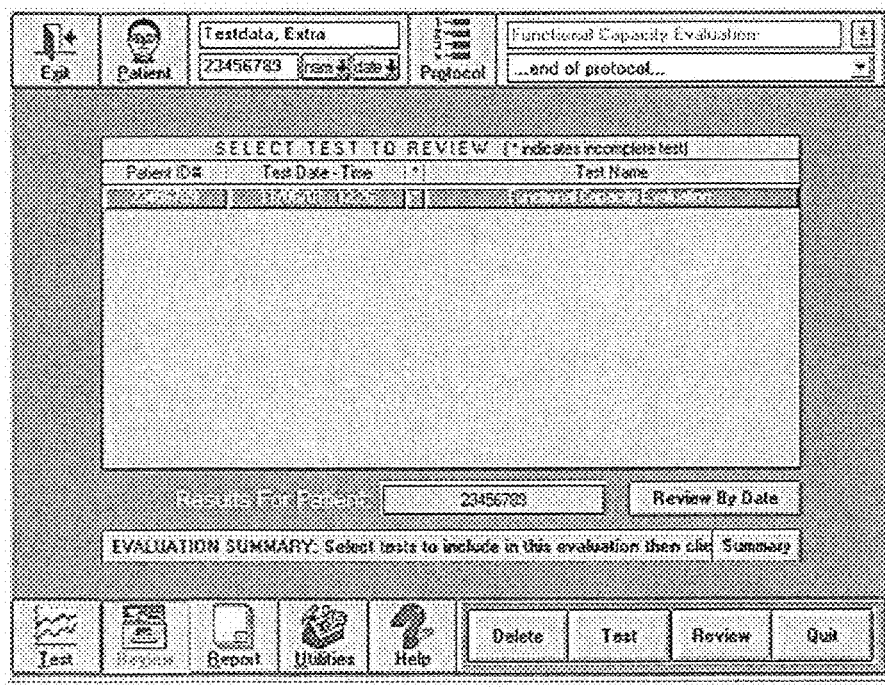
FIG. 66 highlights the "review" button for viewing results after having selected the review file icon button of FIG. 62.
Figure 67:
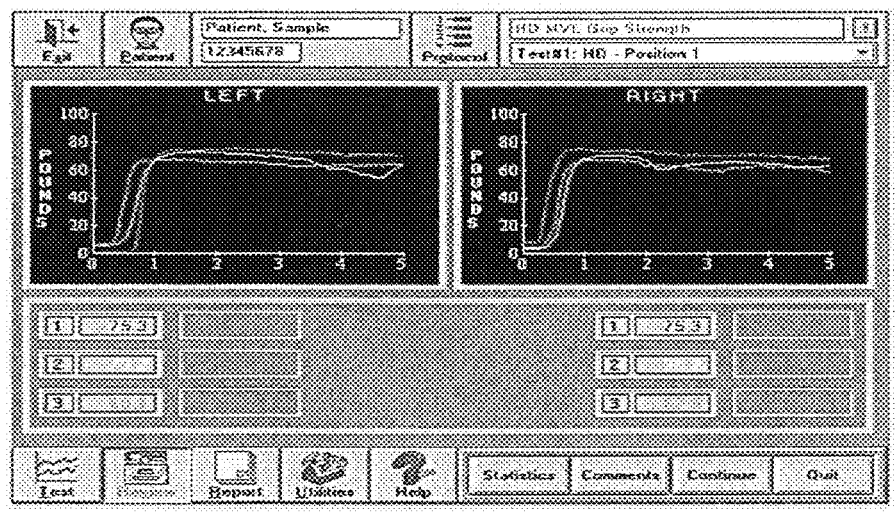
FIG. 67 illustrates the statistics for hand dynamometer testing and button bar changes when selecting a test and using the review button of FIG. 66.
Figure 68:
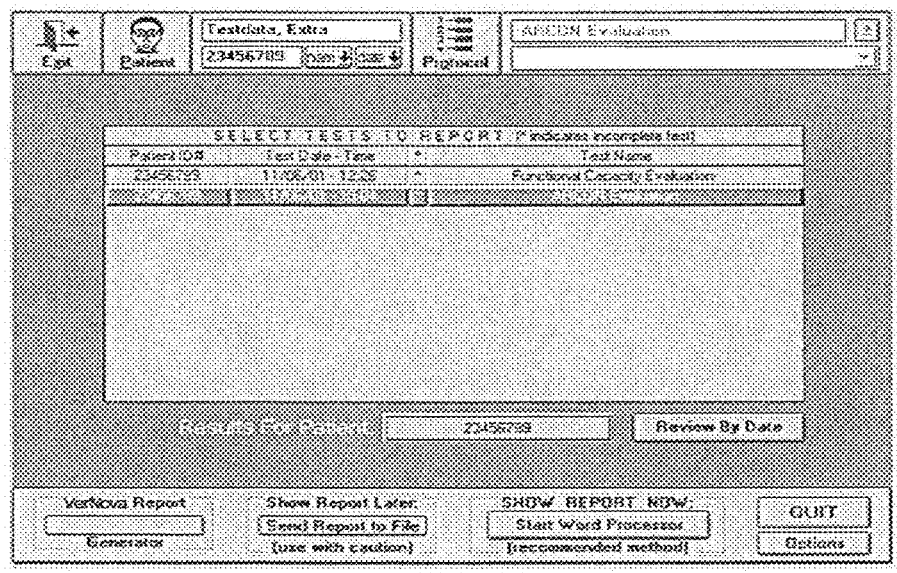
FIG. 68 illustrates the screen that is displayed when the report button of FIG. 33 is selected.

To review the results from a protocol already tested, the protocol may be highlighted, as seen in FIG. 66, and by next clicking the Review button. FIG. 67 shows an example of Hand strength data under review. Clicking the "Statistics" button permits viewing, by the operator, of statistical information. Clicking the Comments button allows the user to review and change any comments and pictures made during testing. Comments and pictures can also be added here if not done before. The user may click the Continue button to review data from the next test in the protocol list. If the screen shows a test that was not completed, an active test screen will come up to run that test as if the user had hit the Test button from the review screen. The Quit button will take the operator back to the review screen. Clicking the report button causes display of the report screen of FIG. 68, with various choices regarding the report.

Figure 69:
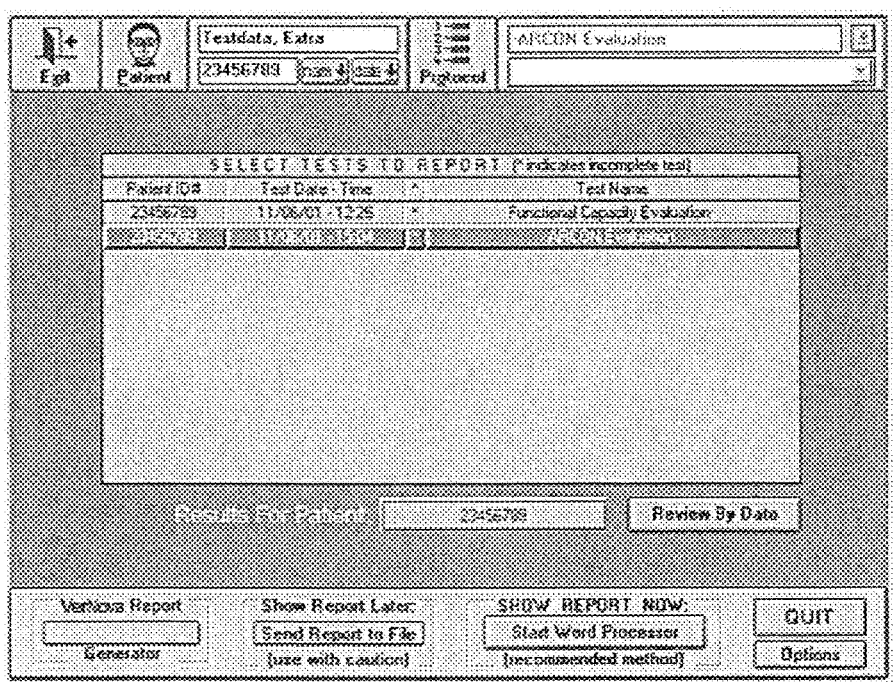
FIG. 69 highlights the option button that may be selected on the button bar to change report options available by the software of the present invention.
Figure 70:
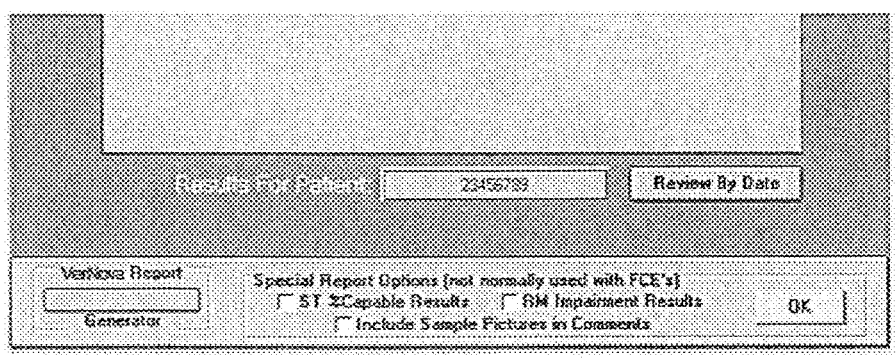
FIG. 70 illustrates the report options that become available on screen when the options button of FIG. 69 is selected.

The Report button is used to generate reports from test results. The system software uses Word for Windows™ as the underlying "engine" for generating reports. The reports are produced using special templates which automate the report generation process. Standard report templates are provided with the system, which may be further customized to suit specific requirements. To change the built-in report generation options, the operator may click on the Options button on the bottom right part of the screen, as seen in FIG. 69, to produce the changes seen in FIG. 70, where the user can check the options at the bottom that he/she wishes to change. The "ST % Capable Results" box may be checked if the user wants to use the Biomechanical Model results for the Static Strength test for the percent capable by the most loaded joint norm. The Default option is to use the Static Strength result for the Physical Demand Characteristic Level for occasional lifting. The "RM Impairment Results" option may be checked if Spinal Range of Motion testing was done and the user wants to include a Spinal Impairment Rating Report. The default is not to include this report. Checking the "Include Sample Pictures in Comments" option will include the sample instruction picture with any comments made without custom pictures. The Default is to not include sample pictures. The operator may click OK to accept any changes. Any changes made in the report options screen will only affect the current report to be generated.

Figure 71:
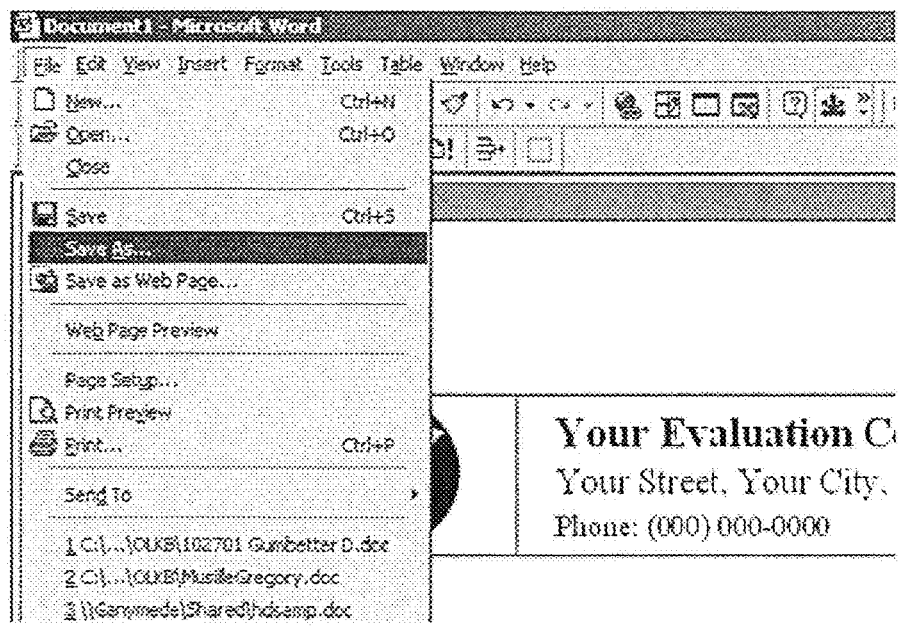
FIG. 71 illustrates the menu options available when seeking to save a report.
Figure 72:
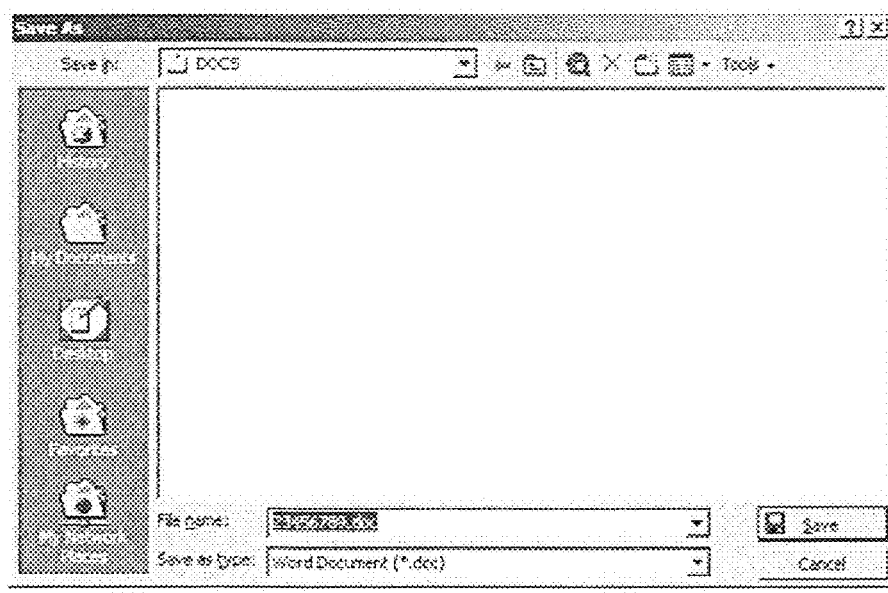
FIG. 72 illustrates the default file name assigned to a saved report document.

The report is generated from information contained in the software databases. As long as the user does not make changes in the MS Word document generated from that data, the same report can be regenerated over and over again. If the user would like to save the MS Word report document for his/her own records or to send the file to a customer service representative for a referral, he may use the following steps. After the report has generated, the user may click the file menu in Word and select Save As, as seen in FIG. 71, to obtain the screen of FIG. 72. The default name of the document will be the patient id number (e.g. 123456789.doc). It is probably a good idea to name the report something a little more meaningful. The default save directory will be X:\ARCON\BD\DOC where X is the drive letter where the software directory resides. This folder is used because it will be part of a full backup of the Professional Healthcare system if one is performed. You can choose to save to another location if you like. When the operator is ready, the Save button may be clicked.

The software of the current invention uses an algorithm to calculate, based on the test results, a coefficient of variation between the results of each test. The results of the testing and the coefficient of variation will appear in a detailed report for each series of tests, as a percentage. Generally, when the percentage is approximately less than 15%, the test is reliable. For a comparison of left-hand and right-hand side testing, dominance is taken into account, but if a percentage difference exceeds 12.5%, it indicates impairment or a deficit. The test results and analysis based upon the variation may appear in an easily scannable format to easily accommodate ready identification by a doctor of functional loss. The scannable format may comprise a table of the average results and normative standards, and may appear a bar chart with color coding of the results. The software also generates on-screen display of the results (FIGS. 95-111).

The software, in accordance with one embodiment of the present invention, may run on an exemplary computer system 200, which is shown schematically in 75, and which may comprise a mobile computing unit 201 interacting with external peripherals 202, such as a separate GPS receiver 241, and interacting with network resources 103, including a PC 261. A complete exemplary computer system will be described for an understanding of how the software may interact with and on mobile computing unit 201, even though at embodiment involving usage of the software may not require each of the described computer components.

The mobile computing unit 201 may include a data bus 224 or other communication mechanism for communicating information across and among various parts of mobile computing unit 201, and a central processing unit ("processor" or CPU) 222 coupled with a bus 224 for processing information and performing other computational and controls tasks. Mobile computing unit 201 may also include a volatile storage 225, such as a random access memory (RAM) or other dynamic storage device, coupled to bus 224 for storing various information as well as instructions to be executed by processor 222. The RAM may be Dynamic Random Access Memory (DRAM), or Static RAM (SRAM), or any other similar type of RAM known in the art. The volatile storage 225 also may be used for storing temporary variables or other intermediate information during execution of instructions by processor 222. Mobile computing unit 201 may further include a read only memory (ROM) or an erasable programmable memory (EPROM) 227 or other static storage device coupled to bus 224 for storing static information and instructions for processor 222, such as basic input-output system (BIOS), as well as various system configuration parameters. A persistent storage device or non-volatile memory 226, such as a magnetic disk, optical disk, or solid-state flash memory device is provided and coupled to bus 224 for storing information and instructions.

Mobile computing unit 201 may be coupled via bus 224 to a touch screen display 221, such as a plasma display, or a liquid crystal display (LCD), for displaying information to a user of the mobile computing unit 201. If desired, the mobile computing unit 201 may also be coupled via bus 224 to an external display screen 245, which may further comprise a cathode ray tube (CRT). An external input device 244, including alphanumeric and other keys, may also be coupled to bus 224 for communicating information and command selections to processor 222. Another type of user input device is cursor control device 243, such as a mouse, a trackball, or cursor direction keys for communicating direction information and command selections to processor 222 and for controlling cursor movement on display 245, if desired. Also, a cursor control device 243 may also be utilized for the PC 261 of the network resources 203.

An external storage device 242 may be connected to the mobile computing unit 201 via bus 224 to provide an extra or removable storage capacity for the mobile computing unit 201. In an embodiment of the computer system 200, the external removable storage device 242 may be used to facilitate exchange of data with other computer systems.

According to one embodiment of the invention, the techniques described herein are performed by mobile computing unit 201 in response to processor 222 executing one or more sequences of one or more instructions contained in the volatile memory 225. Such instructions may be read into volatile memory 225 from another computer-readable medium, such as persistent storage device or non-volatile memory device 226. Execution of the sequences of instructions contained in the volatile memory 225 causes processor 222 to perform the process steps described herein. In alternative embodiments, hard-wired circuitry may be used in place of or in combination with software instructions to implement the invention. Thus, embodiments of the invention are not limited to any specific combination of hardware circuitry and software.

The term "computer-readable medium" as used herein refers to any medium that participates in providing instructions to processor 222 for execution. The computer-readable medium is just one example of a machine-readable medium, which may carry instructions for implementing any of the methods and/or techniques described herein. Such a medium may take many forms, including but not limited to, non-volatile media, volatile media, and transmission media. Non-volatile media includes, for example, optical or magnetic disks, such as storage device 226. Volatile media includes dynamic memory, such as volatile storage 225. Transmission media includes coaxial cables, copper wire and fiber optics, including the wires that comprise data bus 224. Transmission media can also take the form of acoustic or light waves, such as those generated during radio-wave and infra-red data communications.

Common forms of computer-readable media include, for example, a floppy disk, a flexible disk, hard disk, magnetic tape, or any other magnetic medium, a CD-ROM, any other optical medium, punchcards, papertape, any other physical medium with patterns of holes, a RAM, a PROM, an EPROM, a FLASH-EPROM, a flash drive, a memory card, any other memory chip or cartridge, a carrier wave as described hereinafter, or any other medium from which a computer can read.

Various forms of computer readable media may be involved in carrying one or more sequences of one or more instructions to processor 222 for execution. For example, the instructions may initially be carried on a magnetic disk from a remote computer. Alternatively, a remote computer can load the instructions into its dynamic memory and send the instructions over a telephone line using a modem. A modem local to computer system 200 can receive the data on the telephone line. The bus 222 may carry the data to the volatile storage 225, from which processor 222 retrieves and executes the instructions. The instructions received by the volatile memory 225 may optionally be stored on persistent storage device 226 either before or after execution by processor 222. The instructions may also be downloaded into the mobile computing unit 201 via Internet using a variety of network data communication protocols well known in the art.

The mobile computing unit 201 may also include a communication interface, such as network interface card 223 coupled to the data bus 222. Communication interface 223 provides a two-way data communication coupling to a network link that may be connected to a local network 262. For example, communication interface 223 may be an integrated services digital network (ISDN) card or a modem to provide a data communication connection to a corresponding type of telephone line. As another example, communication interface 223 may be a local area network interface card (LAN NIC) to provide a data communication connection to a compatible LAN. Wireless links, such as well-known 802.11a, 802.11b, 802.11g and Bluetooth may also used for network implementation. In any such implementation, communication interface 223 sends and receives electrical, electromagnetic or optical signals that carry digital data streams representing various types of information.

Network link 223 typically provides data communication to other network resources. For example, the network link may provide a connection through local network 262 to a host computer 261, or the mobile computing unit 201 may connect directly to the host computer 261. Alternatively, the network link 223 may connect through gateway/firewall 263 to the wide-area or global network 264, such as an Internet. Thus, the mobile computing unit 201 can access network resources located anywhere on the Internet 264. On the other hand, the mobile computing unit 201 may also be accessed by others, with permission, who are located anywhere on the local area network 262 and/or the Internet 264. The other users may themselves be operating a platform similar to computer system 200.

Local network 262 and the Internet both use electrical, electromagnetic or optical signals that carry digital data streams. The signals through the various networks and the signals on network link and through communication interface 262, which carry the digital data to and from mobile computing unit 201, are exemplary forms of carrier waves transporting the information.

Mobile computing unit 201 can send messages and receive data, including program code, through the variety of network(s) including the Internet 264 and LAN 262, network link and communication interface 233. In the Internet example, when the mobile computing unit 201 acts as a network server, it might transmit a requested code or data for an application program running on PC 261 through the Internet 264, gateway/firewall 263, local area network 262 and communication interface 223. Similarly, it may receive code from other network resources.

The received code may be executed by processor 222 as it is received, and/or stored in persistent or volatile storage devices 226 and 225, respectively, or other non-volatile storage for later execution. In this manner, computer system 200 may obtain application code in the form of a carrier wave.

The present invention is not limited to any specific types of wireless or wired network protocols. A network configuration may be achieved using a variety of known networking protocols.

The examples and descriptions provided merely illustrate a preferred embodiment of the present invention. Those skilled in the art and having the benefit of the present disclosure will appreciate that further embodiments may be implemented with various changes within the scope of the present invention. Other modifications, substitutions, omissions and changes may be made in the design, size, materials used or proportions, operating conditions, assembly sequence, or arrangement or positioning of elements and members of the preferred embodiment without departing from the spirit of this invention.

What is claimed is:

1. A method for displaying assessment information relating to and facilitating determining functional abilities of a patient being determined in a functional evaluation using a plurality of measurement devices and a computer system with displaying of measurements from three test trials out of a maximum of six total trials in a graphical user interface (GUI), the method comprising:

dynamically displaying each of three measurements in a respective plurality of locations in a measurement display region of the GUI, each location in the measurement display region corresponding to a measurement taken in one of three test trials, the three measurements representing strength or range of motion measurements associated with at least one protocol of tests to assess one or more current functional abilities of the patient during the functional evaluation;

dynamically displaying a coefficient of variation in the measurement display region of the GUI, the coefficient of variation representing test validity of the three successive test trials out of the maximum of six total test trials;

displaying a button in said measurement display region configured for toggling for selecting of any said trial measurement in said measurement display region and causing blanking of said selected trial measurement, thereby permitting immediate retesting of said trial, and determining by said system of a revised coefficient of variation for instantaneously determining validity of said measurements; and immediately stopping the functional evaluation when the revised coefficient of variation is above a threshold amount for the three test trials out of a maximum of six test trials;

displaying a test protocol selection GUI comprising a pictorial image of a front side and a back side of a human body for identifying a plurality of body regions, each of said plurality of body regions being selectable for said functional evaluation; and associating a respective protocol of tests with each body region of the plurality of body regions; and in response to a selection of one or more of the body regions by a user input device, displaying of the associated protocol of tests for each of the selected one or more body regions, and providing instructions in an instructions GUI for completing the associated protocol of tests for said functional evaluation.

2. The method of claim 1 further comprising displaying said coefficient of variation using a median of the displayed measurements from the three successive test trials as a comparison value.

3. The method of claim 2 further comprising displaying an impairment rating based on the measurements of the associated protocols of tests, by correlating an average of the displayed measurements to a database of population normative standards, when the coefficient of variation is below the threshold amount.

4. The method of claim 3 further comprising displaying a color-coded bar chart identifying functional loss experienced by the patient, by arranging said comparison value with a respective one of the population normative standards, for each of the associated protocols of tests.

5. The method of claim 4 further comprising printing a report of the assessment information.

6. The method of claim 1 further comprising displaying said coefficient of variation using a mean of the displayed measurements from the three successive test trials as a comparison value.

7. The method of claim 6 further comprising displaying an impairment rating based on the measurements of the associated protocols of tests, by correlating an average of the displayed measurements to a database of population normative standards, when the coefficient of variation is below the threshold amount.

8. The method of claim 7 further comprising displaying a color-coded bar chart identifying functional loss experienced by the patient, by arranging said comparison value with a respective one of the population normative standards, for each of the associated protocols of tests.

9. The method of claim 8 further comprising printing a report of the assessment information.

10. The method of claim 1 further comprising displaying said coefficient of variation using a largest of the displayed measurements from the three successive test trials as a comparison value.

11. The method of claim 10 further comprising displaying an impairment rating based on the measurements of the associated protocols of tests, by correlating an average of the displayed measurements to a database of population normative standards, when the coefficient of variation is below the threshold amount.

12. The method of claim 11 further comprising displaying a color-coded bar chart identifying functional loss experienced by the patient, by arranging said comparison value with a respective one of the population normative standards, for each of the associated protocols of tests.

13. The method of claim 12 further comprising printing a report of the assessment information.

14. The method of claim 1 further comprising:
dynamically displaying each of said measurements in a respective plurality of locations in a measurement display region of the GUI for each of the left side and right side of the patient;
displaying a test results GUI when said coefficient of variation is within the threshold amount for said three consecutive test trials, said test results GUI including:
displaying a measurement graph in said measurement display region, said measurement graph displaying a real-time result for each of said measurements of said three consecutive test trials, for each of the left and right sides;
displaying a percentage of deficiency between the left side and right side; and
displaying of said coefficient of variation for each of the left and right sides.

* * * * *